(12) United States Patent
Abo-Auda et al.

(10) Patent No.: US 8,591,543 B2
(45) Date of Patent: Nov. 26, 2013

(54) DEVICES AND METHODS FOR CLOSURE OF A PATENT FORAMEN OVALE

(75) Inventors: Wael Abo-Auda, Allen, TX (US); Waleed Abughazaleh, Garland, TX (US)

(73) Assignee: CardioTulip LLC, Allen, TX (US)

( * ) Notice: Subject to any disclaimer, the term of this patent is extended or adjusted under 35 U.S.C. 154(b) by 391 days.

(21) Appl. No.: 13/096,081

(22) Filed: Apr. 28, 2011

(65) Prior Publication Data
US 2012/0277791 A1 Nov. 1, 2012

(51) Int. Cl.
*A61B 17/08* (2006.01)

(52) U.S. Cl.
USPC .......................................... 606/213; 606/151

(58) Field of Classification Search
USPC .......... 606/151, 157, 158, 213, 215, 216, 221
See application file for complete search history.

(56) References Cited

U.S. PATENT DOCUMENTS

| 3,874,388 | A | 4/1975 | King et al. |
| 7,758,611 | B2 | 7/2010 | Kato |
| 7,780,700 | B2 | 8/2010 | Frazier et al. |
| 8,480,709 | B2 * | 7/2013 | Chanduszko et al. ........ 606/213 |
| 2005/0251154 | A1 | 11/2005 | Chanduszko et al. |
| 2006/0241687 | A1 * | 10/2006 | Glaser et al. .................. 606/213 |
| 2007/0032821 | A1 | 2/2007 | Chin-Chen et al. |
| 2007/0179527 | A1 | 8/2007 | Eskuri et al. |
| 2007/0198038 | A1 * | 8/2007 | Cohen et al. .................. 606/151 |
| 2010/0234885 | A1 | 9/2010 | Frazier et al. |
| 2011/0092988 | A1 | 4/2011 | Cohen et al. |

FOREIGN PATENT DOCUMENTS

WO   WO 03/037201 A1   5/2003

OTHER PUBLICATIONS

International Search Report and Written Opinion of the International Searching Authority received in Patent Cooperation Treaty Application No. PCT/US2012/033420, dated Oct. 10, 2012, 16 pages.

* cited by examiner

*Primary Examiner* — Julian W Woo

(74) *Attorney, Agent, or Firm* — Haynes and Boone, LLP

(57) ABSTRACT

The present invention provides devices and methods for closing a physical anomaly comprising two overlapping layers of tissue, such as a patent foramen ovale ("PFO"). A PFO is comprised of two overlapping layers of malformed interatrial septa, the septum primum and the septum secundum, that form a tunnel between the right atrium and the left atrium. The closure device includes two wings connected to a central arm. The device is delivered through the PFO tunnel in a substantially linear configuration such that the central arm is seated within the PFO tunnel, the first wing extends into the right atrium, and the second wing extends into the left atrium. Once implanted, the closure device is reconfigured such that the arm is seated within the PFO tunnel, the first wing folds against the septum secundum, and the second wing folds against the septum primum, thereby sealing the defect.

25 Claims, 18 Drawing Sheets

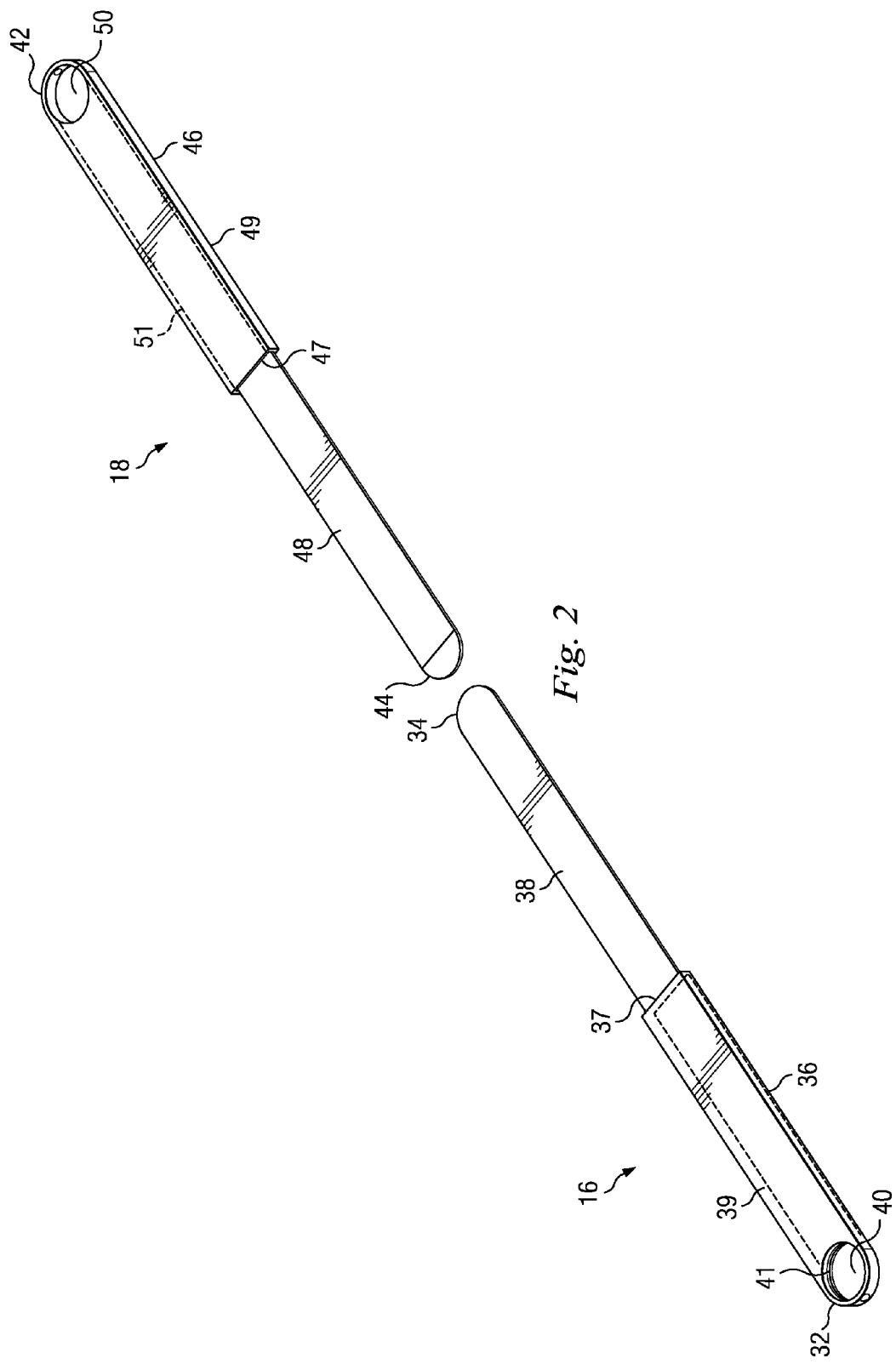

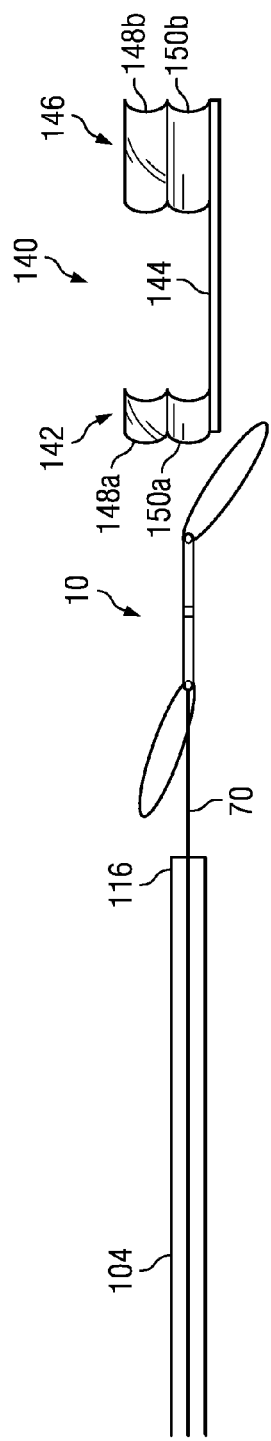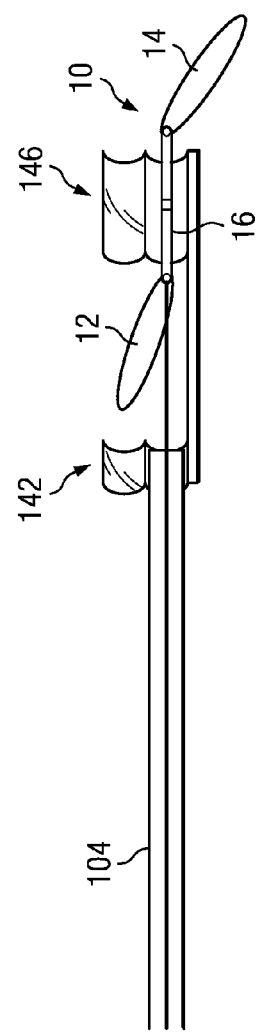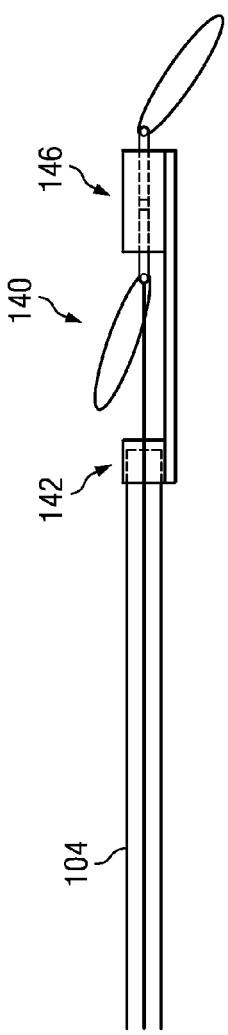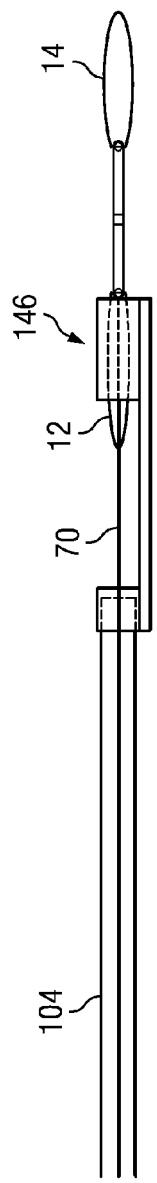
Fig. 11a
Fig. 11b
Fig. 11c
Fig. 11d

DEVICES AND METHODS FOR CLOSURE OF A PATENT FORAMEN OVALE

BACKGROUND

Patent foramen ovale ("PFO") is an anatomical interatrial communication with potential for right-to-left shunting of blood. Specifically, PFO is a flap-like opening between the atrial septa primum and secundum of the heart that persists after one year of age. In utero, the foramen ovale serves as a physiologic conduit for right-to-left shunting of blood in the fetal heart. After birth, with the establishment of pulmonary circulation, the increased left atrial blood flow and pressure presses the septum primum against the walls of the septum secundum, covering the foramen ovale and resulting in functional closure of the foramen ovale. This closure is usually followed by anatomical closure of the foramen ovale due to fusion of the septum primum to the septum secundum.

If anatomical closure of the foramen ovale does not occur, a patent foramen ovale is created. A PFO results when either partial or no fusion of the septum primum and the septum secundum occurs. In the case of partial or no fusion, a persistent passageway or PFO track exists between the septum primum and the septum secundum. The passageway is typically parallel to the plane of the septum primum, and has a mouth that is generally oval in shape. Normally, the passageway is long and quite narrow. Because the mean left atrial pressure is typically higher than the mean right atrial pressure, the opening is usually held closed. However, at times, the mean right atrial pressure may exceed the mean left atrial pressure, causing the PFO track to open and allow the passage of blood (and possible blood clots) from the right atrium to the left atrium (and into systemic circulation). Although the PFO track is often held closed, the endothelialized surfaces of the tissues forming the PFO track prevent the tissues from healing together and permanently closing the PFO track.

Studies have shown that a relatively large percentage of adults have a patent foramen ovale. It is believed that embolism via a PFO may be the cause of a significant number of ischemic strokes, particularly in relatively young patients. Such paradoxical embolism via PFO is considered in the diagnosis of patients who have suffered a stroke or transient ischemic attack ("TIA") in the presence of a PFO and without another identified cause of ischemic attack. Blood clots that form in the venous circulation can embolize, and may enter the arterial circulation via the PFO, subsequently entering the cerebral circulation, resulting in an embolic stroke. Blood clots may also form in the vicinity of the PFO, and embolize into the arterial circulation and into the cerebral circulation. Patients suffering a cryptogenic stroke or TIA in the presence of a PFO are often considered for medical therapy to reduce the risk of a recurrent embolic event. Pharmacological therapy often includes oral anticoagulants or antiplatelet agents to block the formation of emboli. If pharmacotherapy is unsuitable, open heart surgery may be employed to close a PFO with stitches, for example. Like other open surgical procedures, this surgery is highly invasive, risky, requires general anesthesia, and may result in a lengthy recuperation.

Nonsurgical closure of a PFO is possible with umbrella-like devices and a variety of similar mechanical closure devices originally developed for percutaneous closure of atrial septal defects ("ASD"), a condition where the septum primum is often under-developed and perforated. Many of the devices used for closure of an ASD, however, are often technically complex to manufacture and assemble, have a high septal profile, are difficult to deploy to a precise location, and are difficult to implant without deforming the atrial septa and PFO track. In addition, such devices may be difficult or impossible to reposition or retrieve in cases where the original positioning was unsatisfactory. Moreover, these devices are specially designed to close ASDs, or hole-like defects, and therefore are not optimally designed to close and seal a PFO, an overlapping, flap-like, passageway defect. Thus, when inserting an ASD device to close a PFO, the narrow opening and thin flap may form impediments to proper deployment of the device, resulting in residual leakage through the PFO. Even if an occlusive seal is formed, the device may be deployed in the PFO track at an angle, leaving some components insecurely seated against the septum and thereby increasing the risk of thrombus formation due to hemodynamic disturbances.

Accordingly, there exists a need for instrumentation and techniques that facilitate more effective and efficient closure of aberrant, flap-like bodily openings such as patent foramen ovales.

SUMMARY

This disclosure relates to a closure device for closing physical anomalies and defects, including a patent foramen ovale, an atrial septal defect, and various other septal and vascular defects.

In one exemplary aspect, the present disclosure is directed to a device for closing a patent foramen ovale (PFO). The device may comprise a first arm, a second arm, a first wing, and a second wing. The first arm may include a first body portion and a first tab portion, wherein the first body portion may include a first passage extending longitudinally therethrough. The second arm may include a second body portion and a second tab portion, wherein the second body portion may include a second passage extending longitudinally therethrough. The second passage may be sized to slidably receive the first tab portion and the first passage may be sized to slidably receive the second tab portion. The first wing may be pivotally connected to the first arm and the second wing may be pivotally connected to the second arm.

In another exemplary aspect, the present disclosure is directed to a device for closing a patent foramen ovale (PFO). The device may comprise a first arm and a second arm. The first arm may include proximal and distal ends, wherein the proximal end is pivotally connected to a first wing via a first hinge and the first hinge includes a first projection. The second arm may include proximal and distal ends, wherein the proximal end is pivotally connected to a second wing via a second hinge and the second hinge includes a second projection. The distal end of the first arm may be configured to engage the second projection to pivot the second wing with respect to the second arm, and the distal end of the second arm may be configured to engage the first projection to pivot the first wing with respect to the first arm.

In another exemplary aspect, the present disclosure is directed to a system for closing a patent foramen ovale (PFO) in a heart. The system may comprise a delivery catheter, a closure device, an outer tool, and an inner tool. The delivery catheter may have a lumen extending along a longitudinal axis. The closure device may be configured for delivery into the heart and for collapsible containment within the lumen. The closure device may comprise a first arm, a second arm, a first wing, and a second wing. The first arm may include a first body portion and a first tab portion, wherein the first body portion may include a first passage extending longitudinally therethrough. The second arm may include a second body portion and a second tab portion, wherein the second body portion may include a second passage extending longitudinally therethrough. The second passage may be sized to slidably receive the first tab portion and the first passage may be sized to slidably receive the second tab portion. The first wing may be pivotally connected to the first arm and the second wing may be pivotally connected to the second arm. The outer tool may be configured for attachment to the first body portion and have a lumen extending longitudinally through its length. The inner tool may be configured for attachment to the second tab portion. The lumen of the outer tool may be sized to receive a portion of the inner tool, wherein the inner tool is movable with respect to the outer tool to slide the second tab portion with respect to the first passage.

In another exemplary aspect, the present disclosure is directed to a system for closing a patent foramen ovale (PFO) in a heart. The system may comprise a delivery catheter, a closure device, an outer tool, and an inner tool. The delivery catheter may have a lumen extending along a longitudinal axis. The closure device may be configured for delivery into the heart and for collapsible containment within the lumen. The closure device may comprise a first arm and a second arm. The first arm may include proximal and distal ends, wherein the proximal end is pivotally connected to a first wing via a first hinge and the first hinge includes a first projection. The second arm may include proximal and distal ends, wherein the proximal end is pivotally connected to a second wing via a second hinge and the second hinge includes a second projection. The distal end of the first arm may be configured to engage the second projection to pivot the second wing with respect to the second arm, and the distal end of the second arm may be configured to engage the first projection to pivot the first wing with respect to the first arm. The outer tool may be configured for attachment to the proximal end of the first arm and have a lumen extending longitudinally through its length. The inner tool may be configured for attachment to the distal end of the second arm. The lumen of the outer tool may be sized to receive a portion of the inner tool, wherein the inner tool is movable with respect to the outer tool to slide the distal end of the second arm with respect to the first hinge.

In another exemplary aspect, the present disclosure is directed to a method for closing a patent foramen ovale (PFO) in a heart, where the PFO comprises a lumen between a septum primum and a septum secundum. The method may include the steps of: providing a closure device comprising a first wing, a first arm, a second arm, and a second wing; providing an assembly sheath having a lumen extending longitudinally through its length, the lumen sized and configured to contain the closure device in a collapsed configuration; providing a delivery catheter having a lumen extending longitudinally through its length, the lumen sized and configured to contain the assembly sheath; inserting the closure device into the lumen of the assembly sheath such that the closure device is in a collapsed configuration; advancing the delivery catheter into a desired location within the heart; connecting the assembly sheath to the delivery catheter; advancing the closure device through the assembly sheath into the delivery sheath; delivering the closure device at least partially within the PFO; withdrawing the delivery catheter such that the first arm and the second arm are positioned within the lumen of the PFO, the second wing is positioned in a left atrium of the heart, and the first wing is positioned in a right atrium of the heart; rotating the closure device such that the first wing and the second wing are about parallel to the septum secundum and the septum primum, respectively; and interlocking the first arm and second arm such that the second wing is positioned against the septum primum and the first wing is positioned against the septum secundum, wherein the first wing and the second wing exert force on the septum secundum and septum primum, respectively, to push overlapping layers of the septum secundum and the septum primum together to close the PFO.

In another exemplary aspect, the present disclosure is directed to a method for closing a patent foramen ovale (PFO) between a septum primum and a septum secundum. The method may include the steps of: providing a first closure component including a first body portion connected between a first tab and a first wing, the first body portion including a first passage extending longitudinally therethrough; providing a second closure component including a second body portion connected between a second tab and a second wing, the second body portion including a second passage extending longitudinally therethrough; positioning the first and second body and tab portions into the patent foramen ovale; sliding the second tab portion within the first passage; sliding the first tab portion within the second passage; engaging the septum primum between the first and second body portions and the first wing; and engaging the septum secundum between the first and second body portions and the second wing.

In another exemplary aspect, the present disclosure is directed to a method for closing a patent foramen ovale (PFO) between a septum primum and a septum secundum. The method may include the steps of: providing a first arm with proximal and distal ends, the proximal end pivotally connected to a first wing via a first hinge, the first hinge including a first projection; providing a second arm with proximal and distal ends, the proximal end pivotally connected to a second wing via a second hinge, the second hinge including a second projection; engaging the distal end of the first arm with the second projection to rotate the second wing with respect to the second arm; and engaging the distal end of the second arm with the first projection to rotate the first wing with respect to the first arm.

Further aspects, forms, embodiments, objects, features, benefits, and advantages of the present invention shall become apparent from the detailed drawings and descriptions provided herein.

BRIEF DESCRIPTION OF THE DRAWINGS

Aspects of the present disclosure are best understood from the following detailed description when read with the accompanying figures. It is emphasized that various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

FIG. 2 is an exploded view of the arms of the first embodiment of the closure device.

FIG. 3a is a perspective view, and FIGS. 3b-3c are cross-sectional side views.

FIG. 4 is a perspective view of outer and inner connector members attached to portions of the first arm and the second arm, respectively.

FIGS. 11a-11i are partial cross-sectional views illustrating a second embodiment of a compression apparatus and the preparation of a first embodiment of the closure device for delivery.

DETAILED DESCRIPTION

Figure 1:
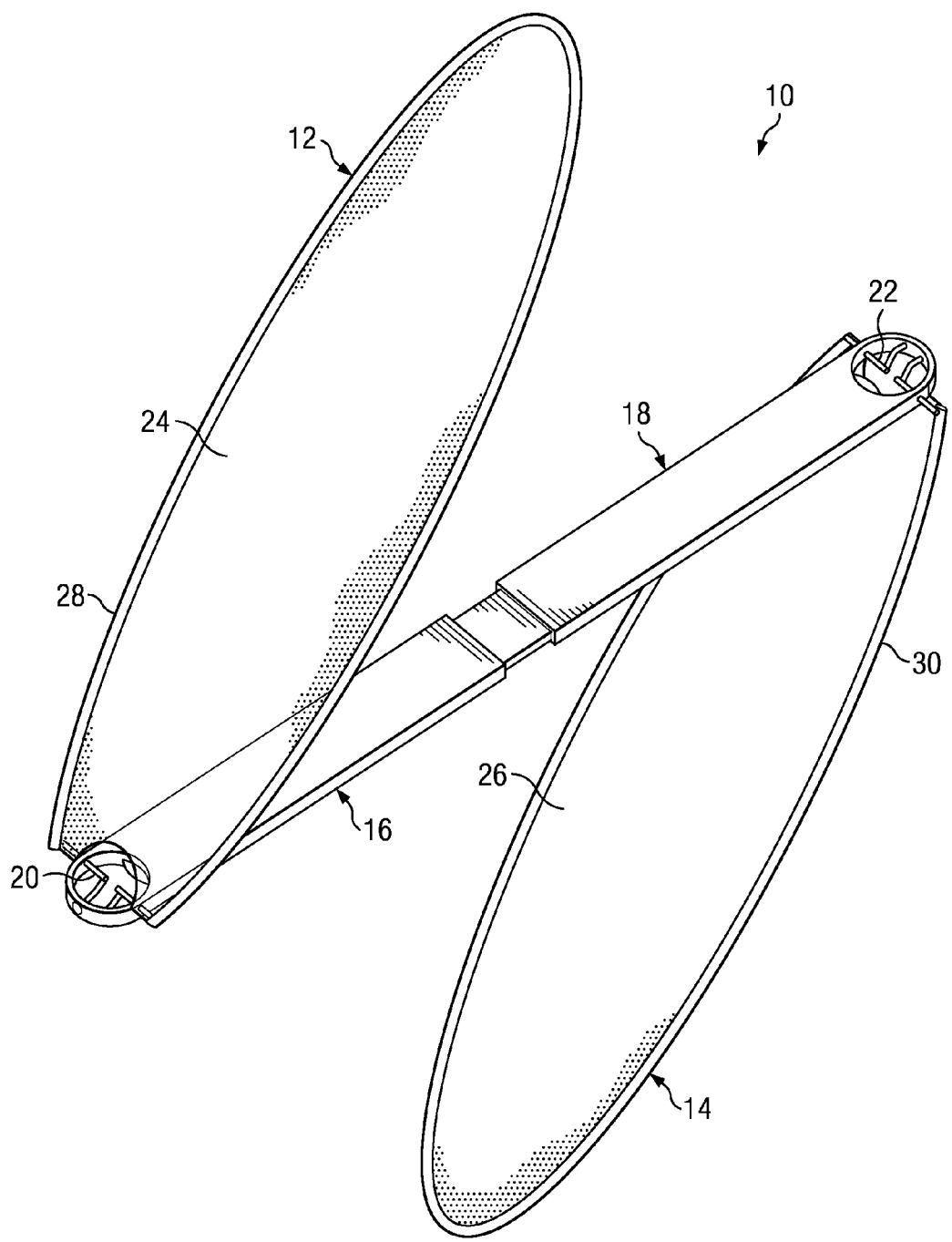
FIG. 1 is a perspective view of a first embodiment of the closure device.

For the purposes of promoting an understanding of the principles of the invention, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention relates to a system and method for closing overlapping layers of tissue in a human or animal body. The various figures show embodiments of a closure device and methods of assembling and using the device to close a patent foramen ovale ("PFO") in a patient's heart. One of ordinary skill in the art, however, would understand that similar embodiments could be used to close other passageways and openings in the body without departing from the general intent or teachings of the present invention.

FIG. 1 illustrates a closure device 10 according to an exemplary embodiment of the present invention for closing a PFO. The closure device 10 includes a pair of wings 12, 14 and a pair of arms 16, 18. The wing 12 is connected to the arm 16 via a hinge mechanism 20, and the wing 14 is connected to the arm 18 via a hinge mechanism 22.

The wings 12, 14 each include sheets 24, 26, respectively, bordered by support frames 28, 30, respectively, having a predetermined shape configuration. The wings 12, 14 are expandable from an unexpanded configuration to an expanded configuration. The wings 12, 14 are constructed from structurally deformable materials that can elastically or plastically deform without compromising their integrity. The sheets are preferably made from a deformable biocompatible material. The sheets 24, 26 span smoothly and continuously across the support frames 28, 30, respectively. The support frames 28, 30 may be made from a self-expanding biocompatible material, such as Nitinol or a resilient polymer, or an elastically compressed spring temper biocompatible material. Other materials having shape memory characteristics, such as particular metal alloys, may also be used. The shape memory materials allow the wings 12, 14 to be restrained in a low profile configuration during delivery and to resume and maintain their expanded shape in vivo after the delivery process.

In the pictured embodiment in FIG. 1, the wings 12, 14 assume the predetermined shape of flat ellipses in the expanded state. The flat and substantially elliptical shape of the wings 12, 14 should not be considered a limiting feature of the invention, as other shapes and configurations of the wings 12, 14 are contemplated for other embodiments of the present invention. These may include, for example, round, rectangular, oblong, triangular, and square shapes for the frames 28, 30, and flat or curved configurations for the sheets 24, 26.

FIG. 2 illustrates the arm 16 and the arm 18 being of substantially identical size and shape. In this embodiment, the arm 16 is shaped like an oblong paddle having a rounded end 32 and a rounded end 34. The arm 16 includes a body portion 36 integrally and rigidly connected to a tab portion 38. The arm 16 includes an upper surface 39. In some embodiments, the body portion 36 and the tab portion 38 may share a continuous upper surface. The body portion 36 includes an aperture 40 extending from the upper surface 39 through the body portion and includes a passage 41 extending longitudinally through the body portion from an opening 37 to the aperture 40. The body portion 36 is generally thicker than the tab portion 38. In this embodiment, the aperture 40 is generally circular and sized for a portion of the hinge mechanism 20 to operate therein. In other embodiments, the aperture may have other shapes such as a square or an oval.

The arm 18 is also shaped like an oblong paddle and includes a rounded end 42 and a rounded end 44. The arm 18 includes a body portion 46 integrally and rigidly connected to a tab portion 48. The arm 18 includes a lower surface 49. In some embodiments, the body portion 46 and the tab portion 48 may share a continuous lower surface. The body portion 46 includes an aperture 50 extending from the lower surface 49 through the body portion and includes a passage 51 extending longitudinally through the body portion from an opening 47 to the aperture 50. The body portion 46 is generally thicker than the tab portion 48. In this embodiment, the aperture 50 is generally circular and sized for a portion of the hinge mechanism 22 to operate therein. In other embodiments, the aperture may have other shapes such as a square or an oval.

The surfaces 39, 49 of the arms 16, 18, respectively, can be smooth or textured. A textured or rough exterior surface may produce an inflammatory response upon contact with the septal tissue in vivo, thereby promoting faster tissue ingrowth and closure of the PFO track. Additionally or alternatively, the surfaces 39, 49 of the arms 16, 18, respectively, may be porous to facilitate cell ingrowth. Additionally or alternatively, the surfaces 39, 49 of the arms 16, 18, respectively, may be impregnated or coated with medication to promote cell ingrowth.

Figure 3A:
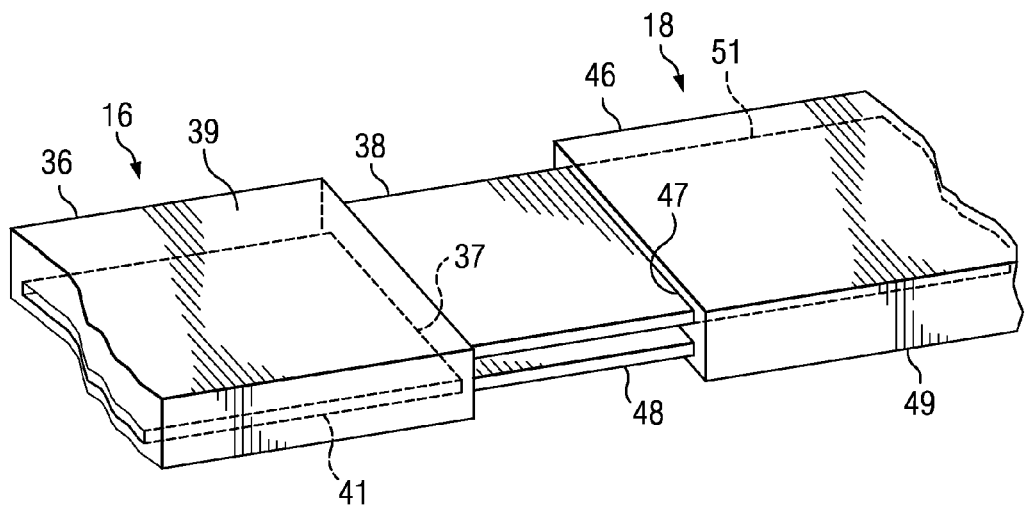
FIGS. 3a-3c are detailed views of the linkage between the arms of the first embodiment of the closure device.

FIG. 3a shows a detailed view of the central interconnection between the arm 16 and the arm 18. The opening 37 of the arm 16 receives the end 44 of the arm 18, and the tab 48 slides into the passage 41. Simultaneously, the opening 47 of the arm 18 receives the end 34 of the arm 16, and the tab 38 slides into the passage 51. The interconnection of the tabs 38, 48 in the passages 51, 41, respectively, causes the tabs to bend slightly inwardly. Thus, when inserted in the passages 51, 41, the tabs 38, 48 exert a slightly outward force against the wall of the passage which serves to frictionally lock the arms 16, 18 in the connected configuration.

Figure 3B:
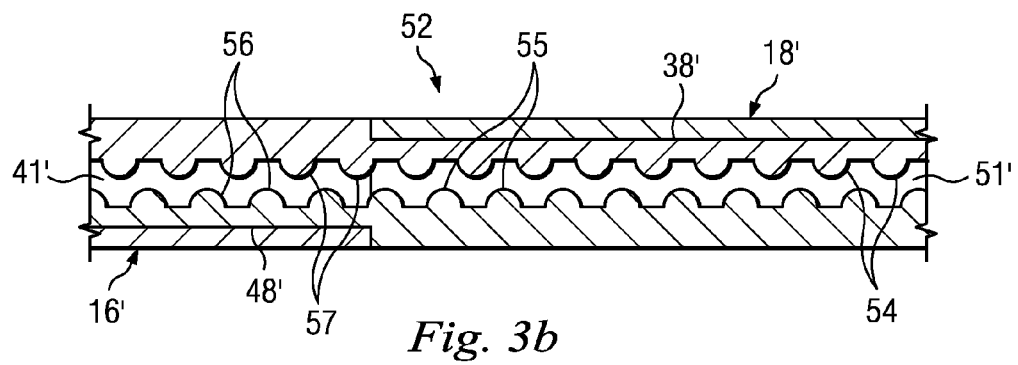

In an alternative embodiment, as shown in FIG. 3b, the arms 16' and 18' are substantially similar to arms 16 and 18 except for the differences to be described. The arms 16' and 18' can be interlocked as described above, but in this embodiment, a releasable locking mechanism 52 further secures the arms 16', 18' together. The locking mechanism 52 includes a set of mechanical connection structures configured as ridges.

The mechanical connection structures comprise a set of ridges 54 extending from tab 38' to interlock with a set of ridges 55 extending from the inferior surface of the passage 51' and a set of ridges 56 extending from tab 48' to interlock with a set of ridges 57 extending from the superior surface of passage 41'. The ridges 54 may also interlock with the ridges 56. The ridges 54, 55, 56, 57 may be shaped to offer more resistance to the arms 16', 18' sliding apart from each other than is offered to the arms 16', 18' sliding toward each other. Nevertheless, the resistance imparted by the locking mechanism may be overcome, by sufficient force, to release the interconnection of the arms 16', 18' and allow the arms 16', 18' to separate.

Figure 3C:
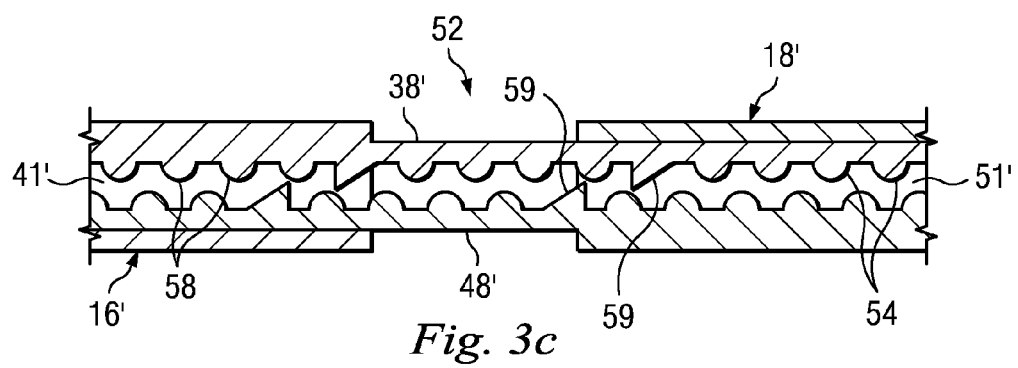

It is understood that the configuration of the releasable locking mechanism can include any of a variety of mechanical connection structures of various sizes, dimensions, shapes, and configurations. In addition, each individual tab 38', 48' and each individual passage 41', 51' may include a variety of mechanical connection structures of various sizes, dimensions, shapes, and configurations. For example, in an alternative embodiment illustrated in FIG. 3c, the mechanical connection structures on each tab 38', 48' and inside each passage 41', 51' may comprise hemispheric protrusions 58 and triangular, teeth-like protrusions 59 to offer more resistance to the arms 16', 18' sliding apart from each other than is offered to the arms 16', 18' sliding toward each other. The resistance imparted by the hemispheric protrusions 58 may be overcome, by sufficient force, to release the interconnection of the arms and allow the arms 16', 18' to partially separate. The triangular protrusions 59, however, are shaped, configured, and positioned to prevent the arms 16', 18' from completely separating. It is understood that the configuration of the releasable locking mechanism can include any of a variety of mechanical connection structures of various sizes, dimensions, shapes, and configurations.

Figure 4:
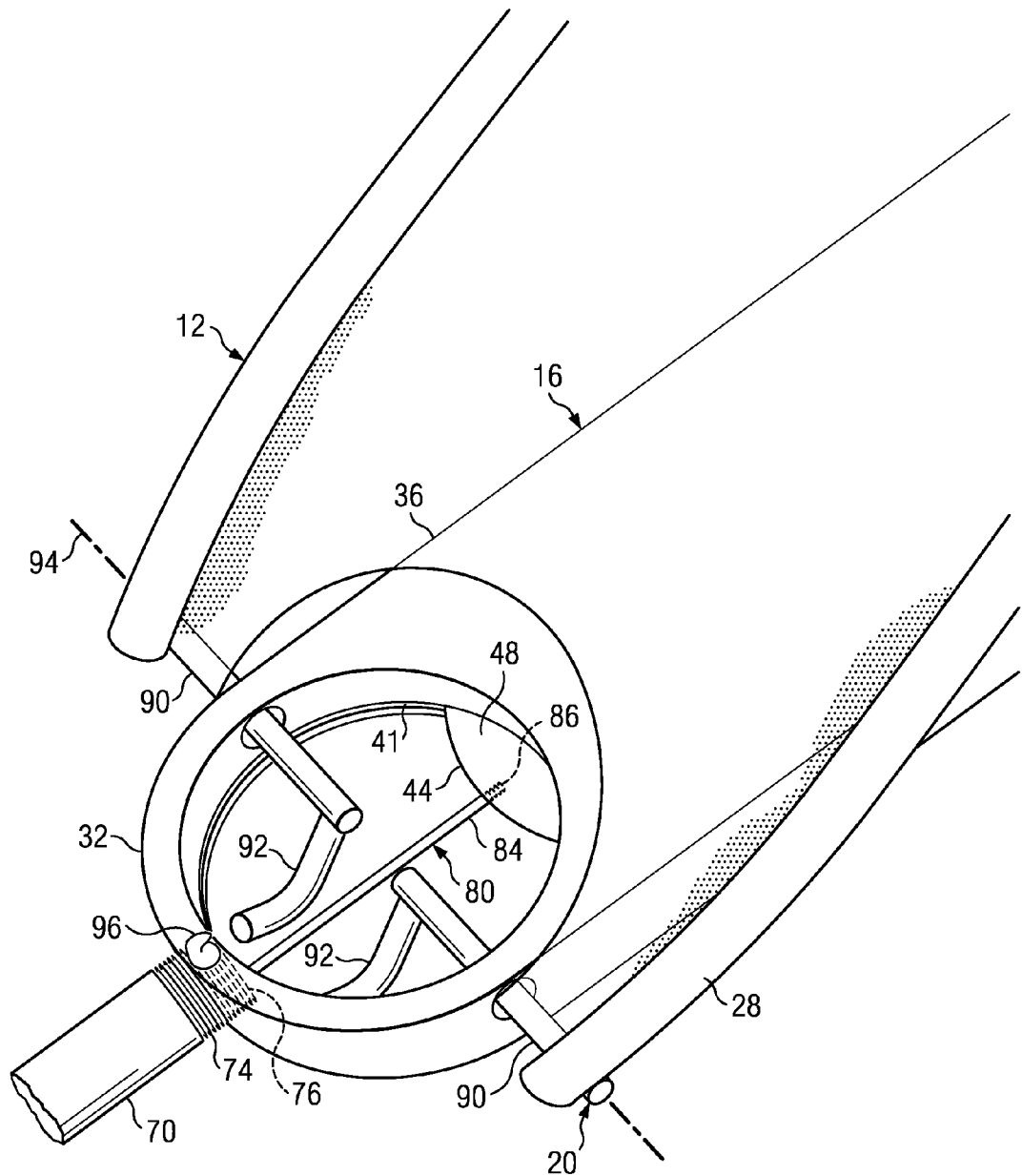
FIG. 4 is a perspective view of a hinge mechanism between the first arm and a first wing of the first embodiment of the closure device. In addition.

FIG. 4 illustrates features of the closure device 10 that slidably draw the arms 16, 18 together and that cause the wings 12, 14 to move. As shown, an outer tool 70 is releasably connected to the body 36 of the arm 16. The outer tool 70 is shaped as a hollow, cylindrical tube having a proximal end 72 (not shown) and a threaded distal end 74. A threaded recess 76 is formed in the end 32 of the arm 16. The outer tool 70 is releasably connected to the arm end 32 by threaded engagement of the threaded distal end 74 of the outer tool in the threaded recess 76. In alternative embodiments, other connectors such as clamps, magnets, or spring-biased connectors may be used to connect the outer tool to the arm 16.

In FIG. 4, an inner tool 80 is shown releasably connected to the end 44 of the arm 18. The inner tool 80 is configured as an elongate structure having a proximal end 82 (not shown) and a threaded distal end 84. In various embodiments, the inner tool can be configured as a cable, a wire, or a rod, for example. A threaded recess 86 is formed in the end 44 of the arm 18. The inner tool 80 is releasably connected to the arm end 44 by threaded engagement of the threaded distal end 84 of the inner tool in the threaded recess 86. In alternative embodiments, other connectors such as clamps, magnets, or spring-biased connectors may be used to connect the inner tool to the arm 18. The inner tool 80 is configured to be slidably received within the outer tool 70. As will be explained in further detail below, moving the inner tool 80 within and relative to the outer tool 70 causes the tab 48 to slide within the passage 41 and the tab 38 to slide within the passage 51.

FIG. 4 also illustrates the hinge mechanism 20 attached to the arm 16. The hinge mechanism 20 includes two hinge pins 90 and two hinge tips 92. The two hinge pins 90 are straight, rod-like structures extending through the body 36 and into the aperture 40 of the arm 16 along a longitudinal axis 94. One end of each hinge pin 90 is connected, either integrally or by a mechanical connector, to the support frame 28 of the wing 12, and the opposite end of each hinge pin extends into the aperture 40. Each hinge tip 92 is a projection shaped as a curved rod extending from each hinge pin 90 in a plane transverse or oblique to the axis 94.

The wing 12 is pivotally connected to the arm 16 and rotates around the axis 94 via the hinge mechanism 20. As the physician exerts a pulling force on the proximal end 82 of the inner tool 80, the tab 48 of the arm 18 slides within the passage 41 of the arm 16 in the direction of the pulling force. As the tab 48 slides into the passage 41, the tab 38 of the arm 16 simultaneously slides within the passage 51 of the arm 18, causing the arms 16, 18 to become interconnected. The hinge tips 92 are curved such that when the tab 48 is pulled by the inner tool 80 towards the end 32 of the arm 16, the tab 48 extends into the aperture 40 and contacts convex portions of the curved hinge tips 92 to swivel the hinge tips 92 about the axis 94, thereby causing the hinge pins 90 to rotate about the axis 94. The rotation of the hinge pins 90 causes the simultaneous rotation of the wing 12 toward the arm 16.

The hinge mechanism 22, as shown in FIG. 1, is configured to be substantially identical to the hinge mechanism 20. The hinge mechanism 22 includes two hinge pins and two hinge tips that are substantially identical in both structure and function to the hinge pins 90 and the hinge tips 92. The wing 18 is pivotally connected to the arm 16 via the hinge mechanism 22. When the inner tool 80 is pulled and moved relative to the outer tool 70, the tab 38 of the arm 16 slides within the passage 51 of the arm 18 in the direction opposite of the pulling force. The advancing end 34 of the tab 38 extends into the aperture 50 and contacts convex portions of the curved hinge tips of the hinge mechanism 22 to swivel the hinge tips and thereby cause the hinge pins to rotate. The rotation of hinge mechanism 22 causes the simultaneous rotation of the wing 14 toward the arm 18.

Figure 5:
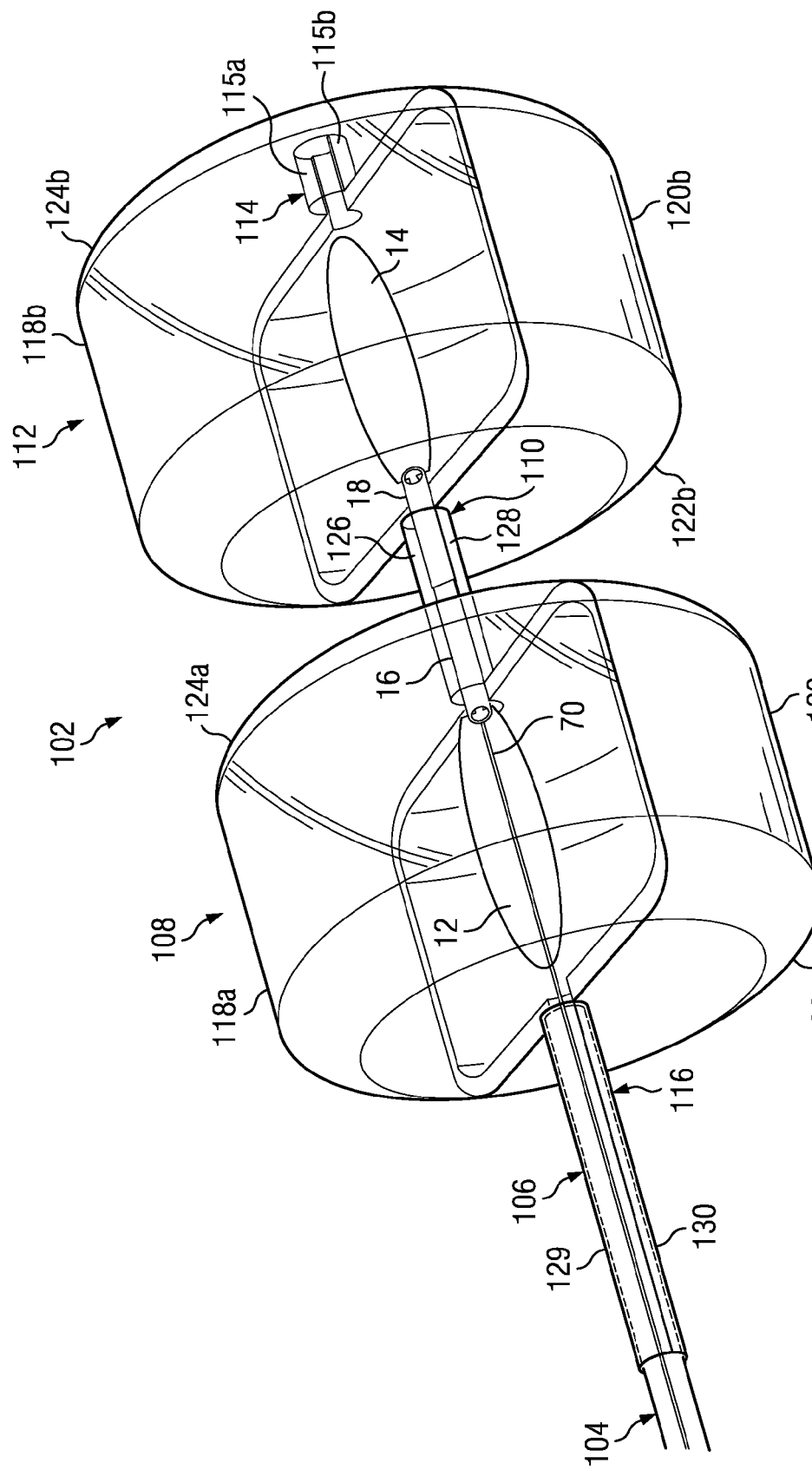
FIGS. 5-10 are perspective views illustrating a first embodiment of a compression apparatus and the preparation of the first embodiment of the closure device for delivery.

In order to introduce the closure device 10 into the atrial chambers through a minimally invasive, percutaneous procedure, the physician first compresses the closure device 10 into a configuration that is sized to pass within a standard intraluminal delivery catheter. FIG. 5 illustrates a dumbbell-shaped compression apparatus 102 designed to compress the closure device 10 into a configuration that is sized for containment within an assembly sheath 104. The compression apparatus 102 includes a proximal tube 106, a proximal container 108, a connecting tube 110, a distal container 112, and a distal flush port 114. The assembly sheath 104 is an elongate, cylindrical, hollow tube having a proximal end (not shown) and a distal end 116. The assembly sheath 104 is sized and configured to receive and contain the closure device 10 in a compressed state. The diameter of the assembly sheath 104 is sized such that the assembly sheath can flushly slide within the proximal tube 106, but cannot advance into the connecting tube 110. The distal end 116 of the assembly sheath 104 is removably and slidably engagable with the proximal tube 106. The assembly sheath 104 possesses sufficient flexibility to flushly slide inside the proximal tube 106, but also possesses sufficient axial stiffness to maintain the closure device 10 in a compressed state and to easily advance into a delivery sheath.

The proximal container 108 and the distal container 112 are configured to be substantially identical in size and shape. In the embodiment pictured in FIG. 5, the containers 108, 112 are configured as rigid, hollow cylindrical drums. The containers 108, 112 are sized and configured to contain the closure device 10 in an expanded state. These containers 108,

112 include transparent upper walls 118a, 118b and opaque lower walls 120a, 120b, respectively. The transparent upper walls 118a, 118b are removably or hingedly attached to the opaque lower walls 120a, 120b. The transparent upper walls 118a, 118b allow the physician to visually observe and direct the compression of the closure device 10. The containers 108, 112 each include proximal surfaces 122a, 122b and distal surface 124a, 124b.

The containers 108, 112 are connected by the connecting tube 110, a rigid, cylindrical, hollow tube. The connecting tube 110 is sized and configured to slidably receive the closure device 10 in a compressed state. The connecting tube 110 extends perpendicularly between the distal surface 124a of the proximal container and the proximal surface 122b of the distal container, such that the lumens of the containers 108, 112 and the connecting tube 110 are centrally aligned and contiguous. The connecting tube 110 comprises a transparent hemi-cylindrical upper portion 126 and an opaque hemi-cylindrical lower portion 128 that are integrally connected to the transparent upper walls 118 and the opaque lower walls 120, respectively.

The proximal tube 106 is a rigid, cylindrical, hollow tube extending perpendicularly from the proximal surface 122a of the proximal container 108 such that the proximal tube 106 is coaxial with the connecting tube 110. The proximal tube 106 comprises a transparent hemi-cylindrical upper portion 129 and an opaque hemi-cylindrical lower portion 130 that are integrally connected to the upper wall 118a and to the lower wall 120a, respectively. It is understood that in alternative embodiments, any of the components described as opaque may be transparent or portions of components described as transparent may be opaque. The lumens of the proximal tube 106, the proximal container 108, the connecting tube 110, and the distal container 112 are centrally aligned and contiguous. The proximal tube 106 is sized and configured to slidably receive and introduce the distal end 116 of the assembly sheath 104 into the lumen of the proximal container 108.

The distal flush port 114 is a rigid, cylindrical hollow tube extending from the distal surface 124b of the distal container 112 into the lumen of the distal container 112 such that the distal flush port 114 is coaxial with the connecting tube 110 and the proximal tube 106. The distal flush port 114 comprises a transparent hemi-cylindrical upper portion 115a and an opaque hemi-cylindrical lower portion 115b that are integrally connected to the upper wall 118b and to the lower wall 120b, respectively.

To begin the compression process, the physician first detaches or hingedly separates the upper components 129, 118a, 126, 118b, 115a from the lower components 130, 120a, 128, 120b, 115b respectively. Then the physician inserts the closure device 10 into the compression apparatus 102 such that the arms 16, 18 are seated within the connecting tube 110 and the wings 12, 14 are positioned within the containers 108, 112. Specifically, the wing 12 is positioned within the proximal container 108 and the wing 14 is positioned within the distal container 112. Within the connecting tube 110, the arms 16, 18 are connected such that the tab 48 extends at least partially within the passage 41 and the tab 38 extends at least partially within the passage 51. The outer tool 70 and the inner tool 80 may be connected to the arm 16 and the arm 18, respectively, in the manner described above. It is understood that this connection of the tools to the arms may be performed either before or while the closure device 10 is positioned in the compression apparatus 102. The outer and inner tools 70, 80 extend through the proximal tube 106, and the assembly sheath 104 is advanced over the outer and inner tools 70, 80 and into the proximal tube.

Next, the physician reattaches the upper components 129, 118a, 126, 118b, 115a to the lower components 130, 120a, 128, 120b, 115b of the compression apparatus 102. The interior of the compression apparatus 102 is flushed with saline through the distal flush port 114.

Figure 6:
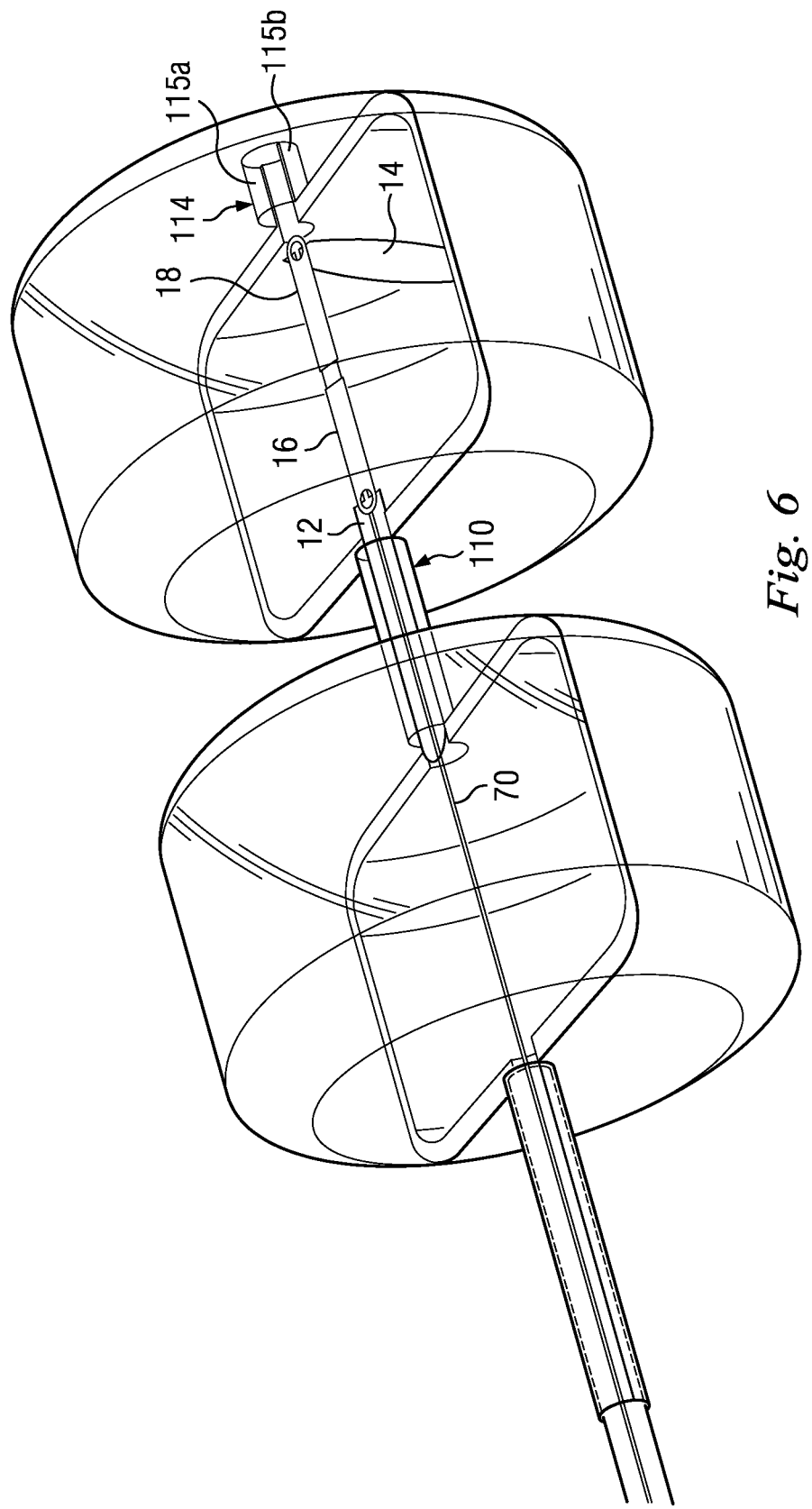

As FIG. 6 illustrates, the compression process proceeds by advancing the outer tool 70 and thus the whole closure device 10 toward the distal flush port 114. The wing 12 is forced to deform into a compressed state as it enters the connecting tube 110 while the wing 14 swings freely in the distal container 112. The assembly sheath 104 is then advanced toward the connecting tube 110 until the assembly sheath abuts the connecting tube 110 within the proximal container 108.

Figure 7:
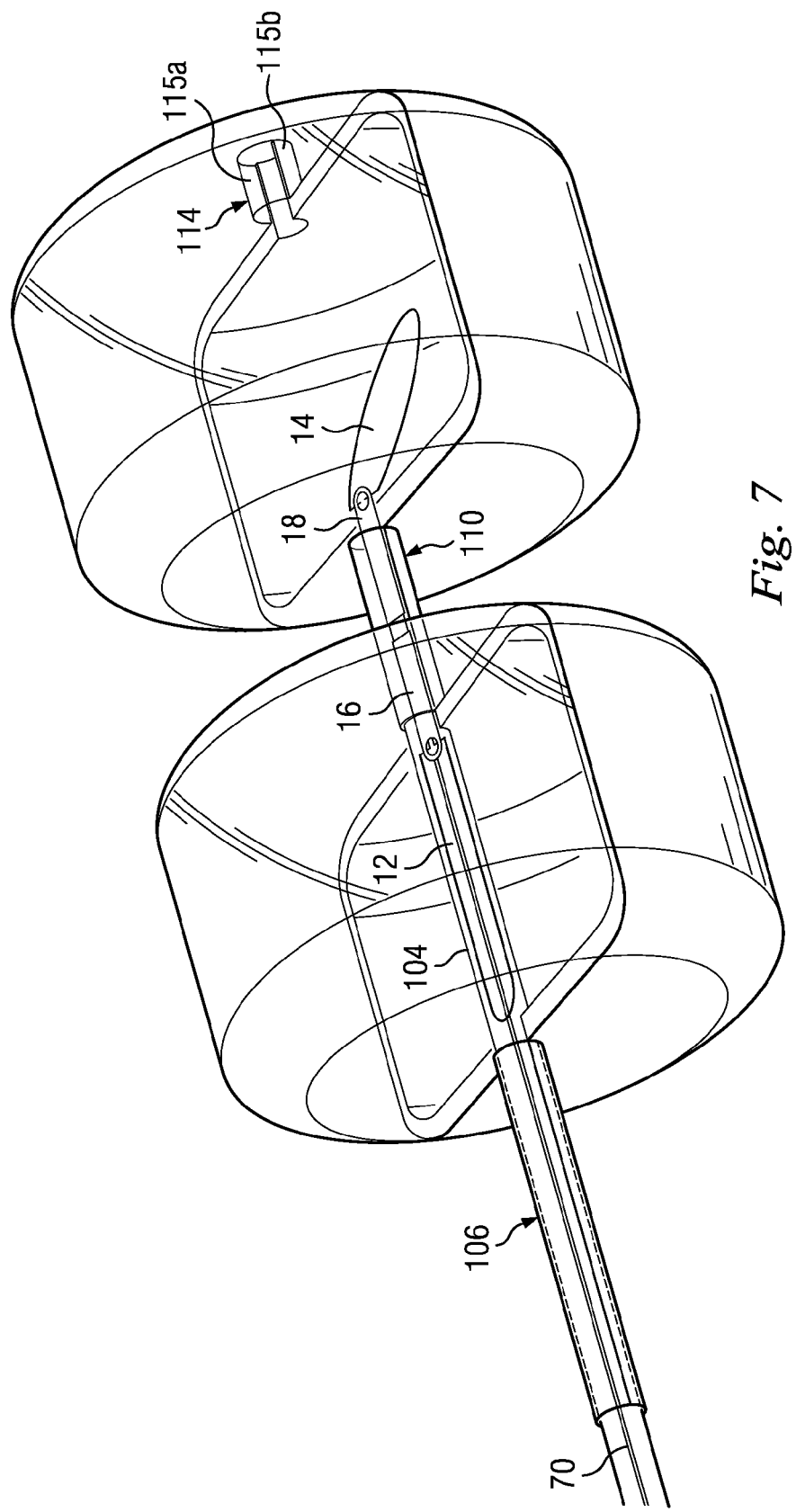

As shown in FIG. 7, when the outer tool 70 is retracted, the wing 12 is drawn from the connecting tube 110 into the assembly sheath 104. The first wing 12 maintains its compressed state as it is drawn into the assembly sheath 104.

Figure 8:
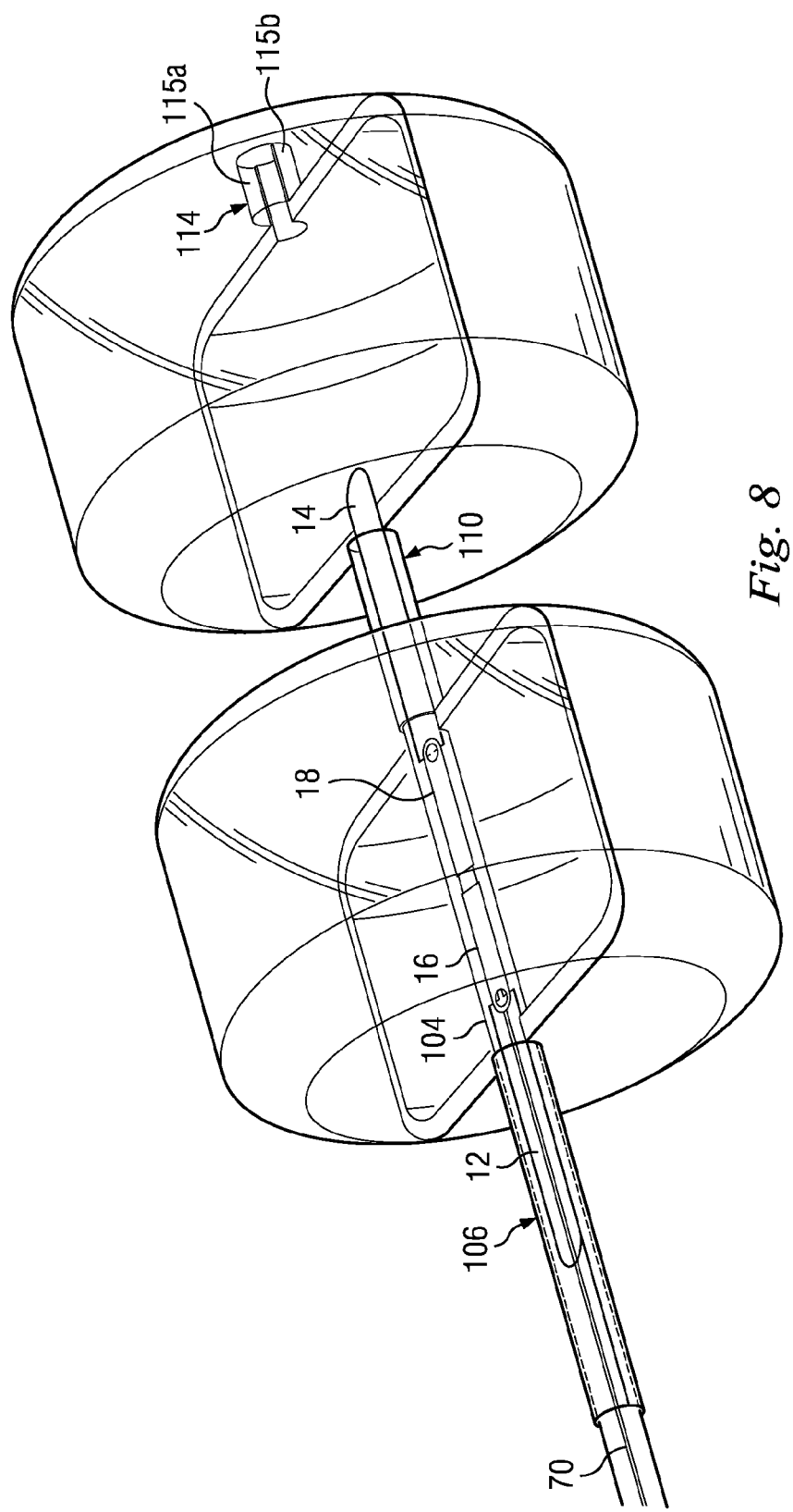

As shown in FIG. 8, the outer tool 70 is further proximally retracted, the arms 16, 18 are drawn through the connecting tube 110 into the assembly sheath 104 and the wing 14 is deformed into a compressed shape as it passes through the connecting tube 110. The wing 14 maintains its compressed state as it is drawn into the assembly sheath 104.

Figure 9:
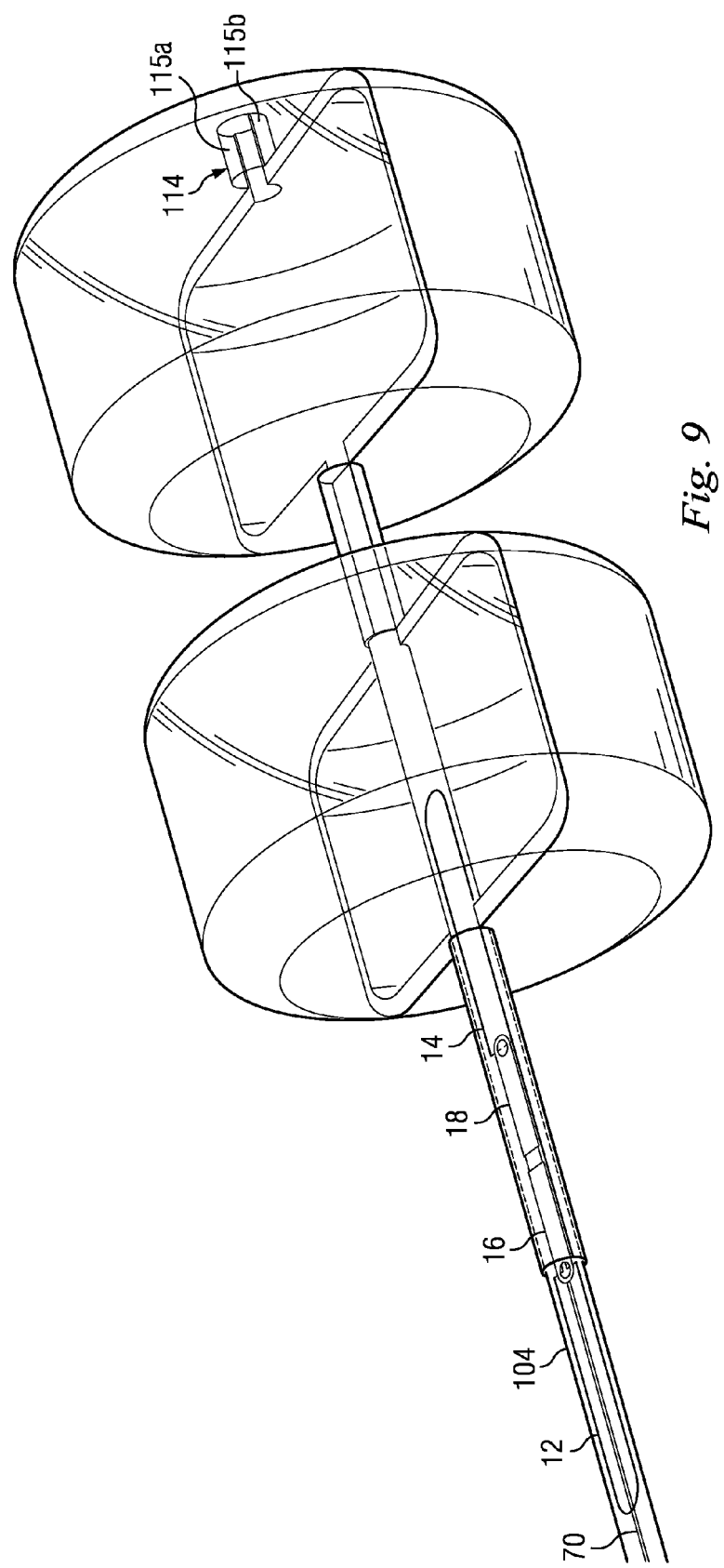

FIG. 9 illustrates the entire closure device 10 positioned inside the assembly sheath 104 with both wings 12, 14 maintained in a compressed state.

Figure 10:
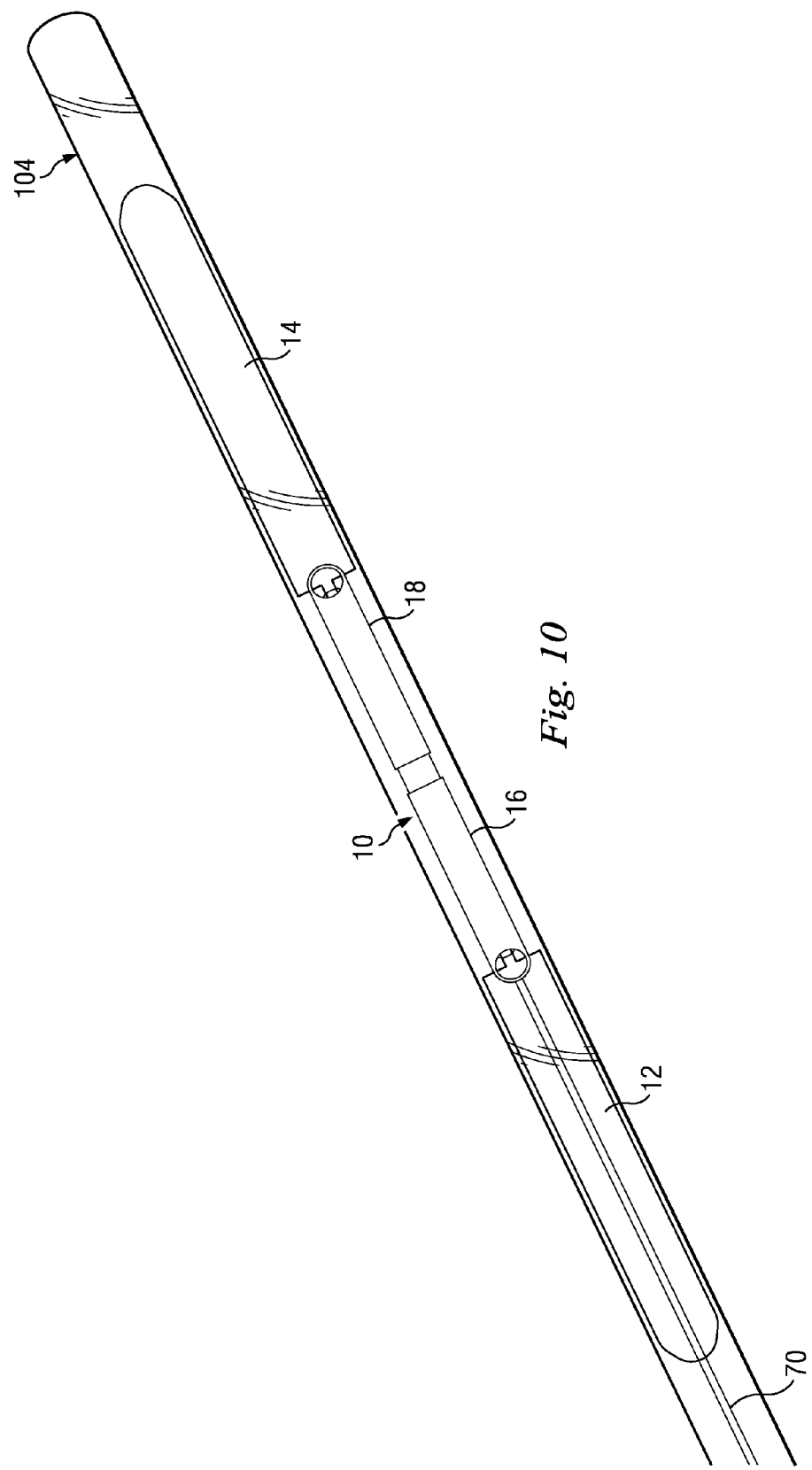

FIG. 10 illustrates the assembly sheath 104 separated from the compression apparatus 102. The assembly sheath 104 contains the closure device 10 in a compressed state.

FIGS. 11a-11i illustrate an alternative embodiment of a compression apparatus and the preparation of the first embodiment of the closure device for delivery. In this embodiment, the compression apparatus 140 includes a proximal tube 142, a connecting bar 144, and a distal tube 146. The diameter of the assembly sheath 104 is sized such that the assembly sheath 104 can flushly slide within the proximal tube 142, but cannot advance into the distal tube 146. The distal end 116 of the assembly sheath 104 is removably and slidably engagable with the proximal tube 142. The assembly sheath 104 possesses sufficient flexibility to flushly slide inside the proximal tube 142 such that the lumen of the assembly sheath 104 is coaxial with the lumen of the proximal tube 142, but also possesses sufficient axial stiffness to maintain the closure device 10 in a compressed state and to easily advance into a delivery sheath.

In the embodiment pictured in FIGS. 11a-11i, the proximal tube 142 and the distal tube 146 are configured as rigid, hollow, cylindrical tubes. The distal tube 146 is sized to have a length substantially similar to the length of the arms 16, 18 of the closure device when the arm 16 is connected to the arm 18. The proximal tube 142 can have a shorter length than the length of the distal tube 146. The proximal tube 142 comprises a transparent hemi-cylindrical upper portion 148a and an opaque hemi-cylindrical lower portion 150a. The distal tube 146 comprises a transparent hemi-cylindrical upper portion 148b and an opaque hemi-cylindrical lower portion 150b. The transparent upper portions 148a, 148b are removably or hingedly attached to the opaque lower portions 150a, 150b, respectively. The transparent upper portions 148a, 148b allow the physician to visually observe and direct the compression of the closure device 10.

The proximal tube 142 and the distal tube 146 are connected by the connecting bar 144, a rigid, elongate bar. The connecting bar 144 is sized to hold both the proximal tube 142 and the distal tube 146 at a distance apart from each other. The opaque lower portions 150a, 150b of the proximal tube 142 and distal tube 146, respectively, are fixedly attached to the connecting bar 144 such that the proximal tube 142 is spaced a distance apart from the distal tube 146 and such that the lumens of the proximal tube 142 and the distal tube 146 are co-axial. The lumens of the assembly sheath 104, the proximal tube 142, and the distal tube 146 are all co-axial.

To begin the compression process, the physician first detaches the transparent hemi-cylindrical upper portions 148a, 148b of the tubes 142, 146 from the opaque hemi-cylindrical lower portions 150a, 150b of the tubes 142, 146, respectively. As shown in FIG. 11b, the physician then places the closure device 10 into the compression apparatus 140 such that the arms 16, 18 are seated within the distal tube 146 and the wings swing freely. Specifically, the wing 12 is positioned within the space between the proximal tube 142 and the distal tube 146, and the wing 14 is positioned distal to the distal tube 146. The outer tool 70 and the inner tool 80 may be connected to the arm 16 and the arm 18, respectively in the manner described above. It is understood that this connection of the tools to the arms may be performed either before or while the closure device 10 is positioned in the compression apparatus 140. Next, as shown in FIG. 11c, the physician reattaches the transparent components 148a, 148b of the compression apparatus 140 to the opaque components 150a, 150b of the compression apparatus 140.

Figure 11E:
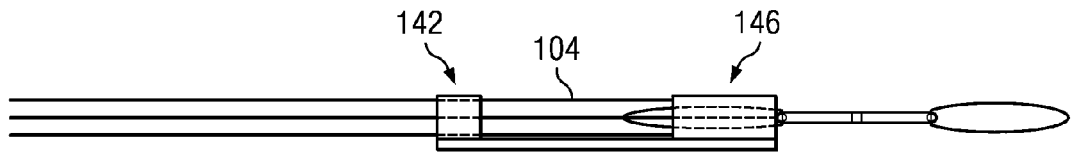

As FIG. 11d illustrates, when the physician advances the outer tool 70 toward the distal tube 146, the outer tool 70 simultaneously advances the wing 12 within the distal tube 146. As the wing 12 advances into the distal tube 146, the wing 12 is forced to deform into a compressed state as it enters the distal tube 146 while the wing 14 swings freely distal to the distal tube 146. FIG. 11e shows that the assembly sheath 104 is then advanced through the proximal tube 142 and toward the distal tube 146 until the assembly sheath 104 abuts the distal tube 146.

Figure 11F:
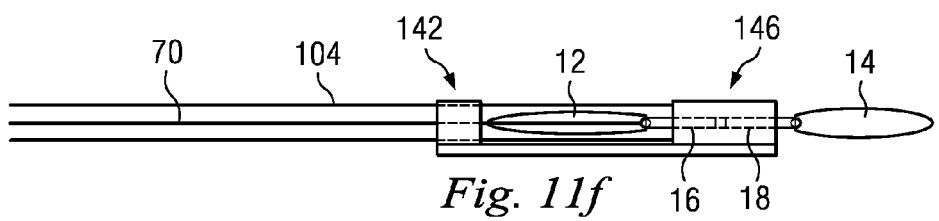
Figure 11G:
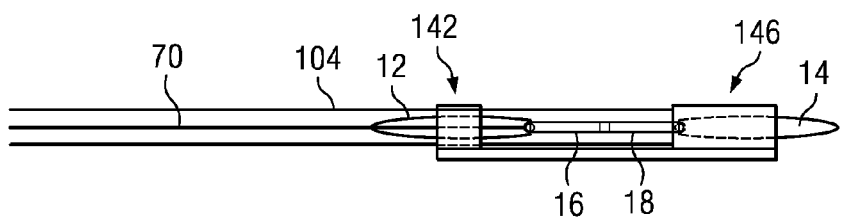

As shown by FIG. 11f, when the physician proximally retracts the outer tool 70, the wing 12 is drawn from the distal tube 146 into the assembly sheath 104 as the arms 16, 18 are drawn back into the distal tube 146. The wing 12 maintains its compressed state as it is drawn into the assembly sheath 104. FIG. 11g illustrates that as the outer tool 70 is further proximally retracted, the arms 16, 18 are drawn through the distal tube 146 into the assembly sheath 104 and the wing 14 is forced to deform into a compressed shape as it passes through the distal tube 146. The wing 14 maintains its compressed state as it is drawn into the assembly sheath 104.

Figure 11H:
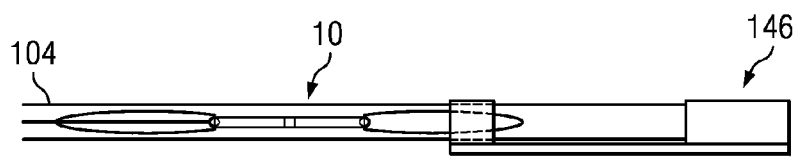

FIG. 11h illustrates the entire closure device 10 positioned inside the assembly sheath 104 with both wings 12, 14 maintained in a compressed state while the assembly sheath is positioned against the distal tube 146.

Figure 11I:
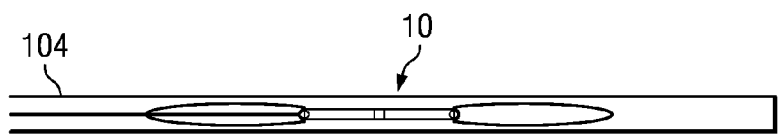

FIG. 11i illustrates the assembly sheath 104 separated from the compression apparatus 140. The assembly sheath 104 contains the closure device 10 in a compressed state.

Figure 12:
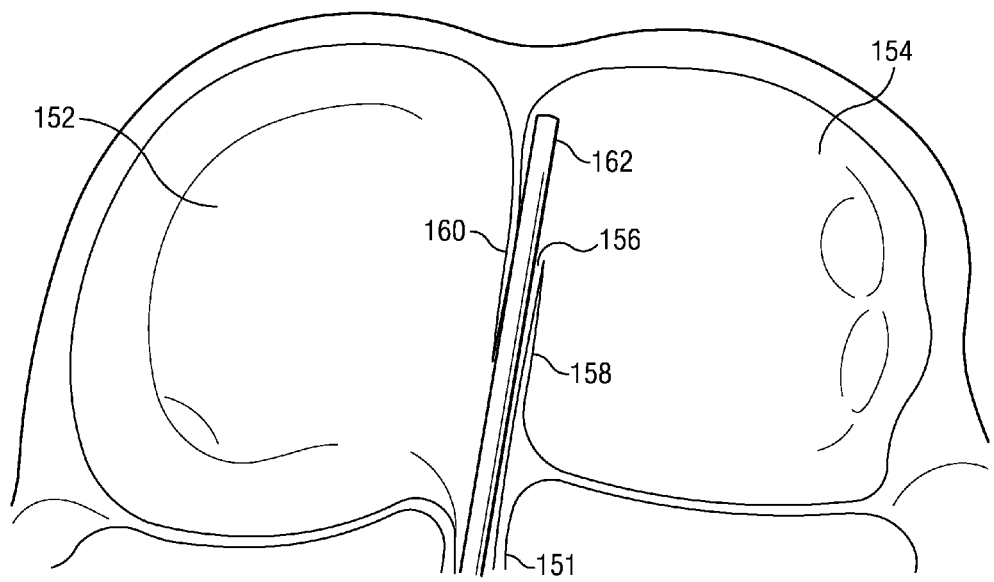
FIGS. 12-15 are schematic views illustrating the delivery of the first embodiment of the closure device within the atria.

With the closure device 10 compressed within the assembly sheath 104 using any of the compression methods described above or known in the art, it is configured for placement within a heart. FIG. 12 shows the two upper chambers in a human heart, the right atrium 152 and the left atrium 154, separated by an interatrial septum containing a PFO track 156. The interatrial septum includes a septum primum 158 and a septum secundum 160. Though the anatomy of PFOs varies widely within the population, the septum primum 158 often extends to and overlaps with the septum secundum 160 as shown in FIG. 12. When a PFO is present, blood may travel through the PFO track 156 between the septum primum 158 and the septum secundum 160.

The closure device 10 is introduced into the atria 152, 154 of the heart, preferably through a minimally invasive, percutaneous procedure. For example, the closure device 10 may be delivered to the atria via percutaneous methods using a delivery catheter. First, a peripheral vein, such as a femoral vein, is punctured with a needle. A wire is inserted through the needle into the vein, and the needle is removed. A dilator and an introducer sheath with at least one hemostatic valve is inserted through the puncture wound, the wire and the dilator are removed, and the sheath is secured in place while maintaining relative hemostasis. With the introducer sheath in place, a catheter containing a guidewire is introduced through the hemostatic valve of the introducer sheath and advanced along the peripheral vein, into the region of the inferior vena cava 151 and the right atrium 152, and into the left atrium 154 through the PFO track 156. The catheter is withdrawn while the guidewire is maintained in place. A delivery sheath 162 and a second dilator are simultaneously introduced into the introducer sheath and advanced over the guidewire to extend from the right atrium 152 into the left atrium 154 through the PFO track 156. The second dilator and the guidewire are then withdrawn. It is understood that alternative procedures and methods may be used to place the delivery sheath 162 into the PFO track 156, between septum primum 158 and a septum secundum 160.

Figure 13:
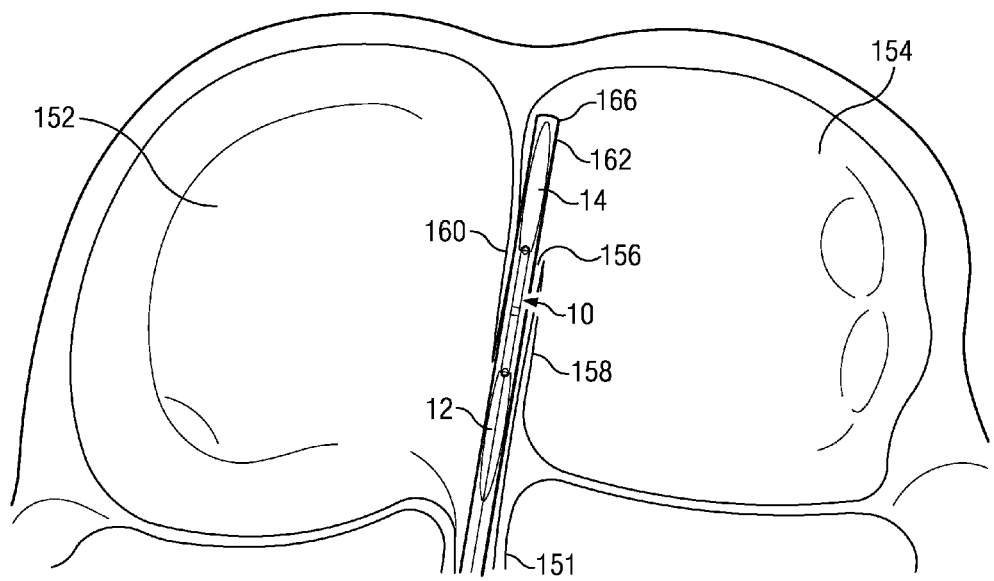

FIG. 13 illustrates the delivery sheath 162, containing the closure device 10, positioned within the PFO track 156 between the septum primum 158 and septum secundum 160. The delivery sheath 162 is an elongate hollow tube with a proximal end 164 and a distal end 166. The distal end 166 of the delivery sheath 162 is positioned within the left atrium 154. The delivery sheath 162 can be a standard delivery sheath as is known in the art or a variation thereof, provided that the delivery sheath 162 is sized to slidably accommodate the closure device 10 in a compressed configuration. The delivery sheath 162 can be constructed of a radiopaque material or carry radiopaque markers. The assembly sheath 104, containing the closure device 10 in a compressed state, is connected to or aligned adjacent to the proximal end 164 of the delivery sheath 162. The compressed closure device 10 is passed through the assembly sheath 104 into the delivery sheath 162 such that the wing 14 of the closure device 10 enters the delivery sheath 162 before the wing 12 of the closure device 10. The closure device 10 is then advanced, still in the compressed configuration, toward the distal end 166 of the delivery sheath 162 until the wing 14 is seated within the distal end 166 of the delivery sheath 162, as shown in FIG. 13. The wing 14 is housed within the distal end of the delivery sheath 162 and positioned within the left atrium 154. The arms 16, 18 of the closure device 10 are housed within the delivery sheath 162 and positioned across the PFO track between the overlapping septum primum 158 and septum secundum 160. The wing 12 is housed within the delivery sheath 162 and positioned within the right atrium 152.

Figure 14:
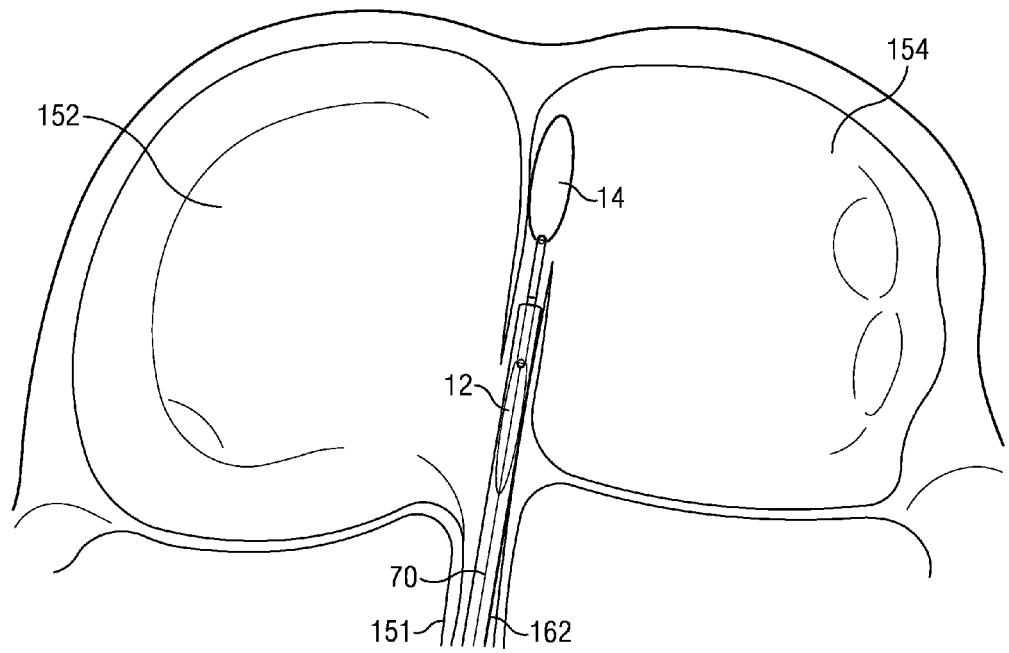

As illustrated in FIG. 14, the closure device 10 is delivered into the atria by withdrawing the delivery sheath 162 from the heart while leaving the closure device 10 in place across the PFO track 156. The delivery sheath 162 is withdrawn from the left atrium 154 into the right atrium 152, and then is withdrawn from the heart entirely. The physician can maintain the position of the closure device 10 by holding the outer tool 70 steady relative to the delivery sheath 162 as the delivery sheath 162 is withdrawn from the heart. As the delivery sheath 162 is withdrawn and the closure device 10 is released from the delivery sheath 162, the wings 12, 14 resume their predetermined expanded configurations in the form of ellipses.

Figure 15:
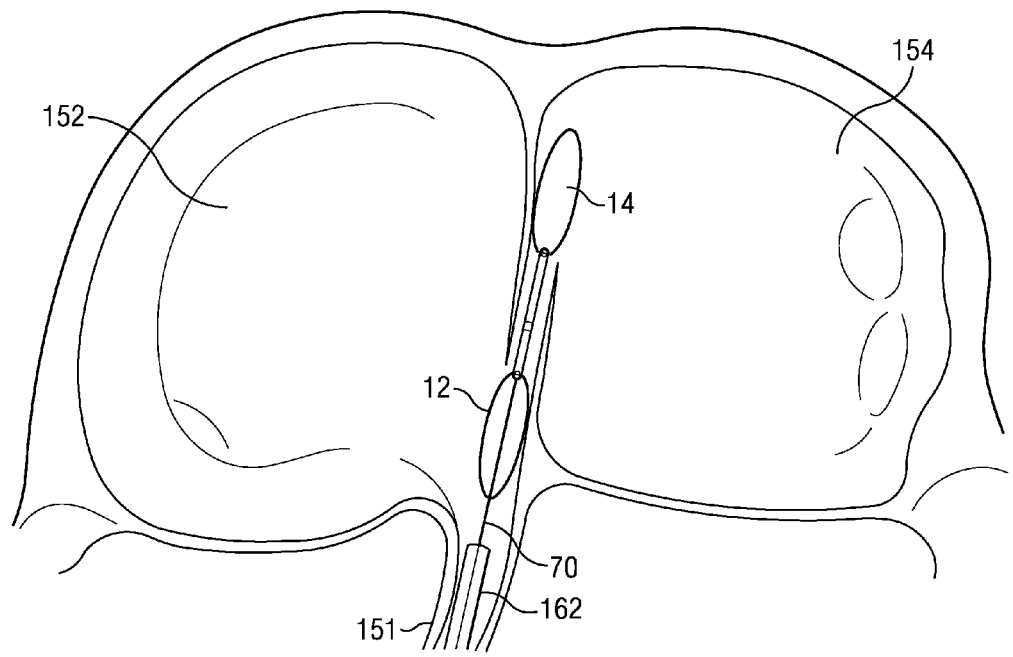
Figure 17:
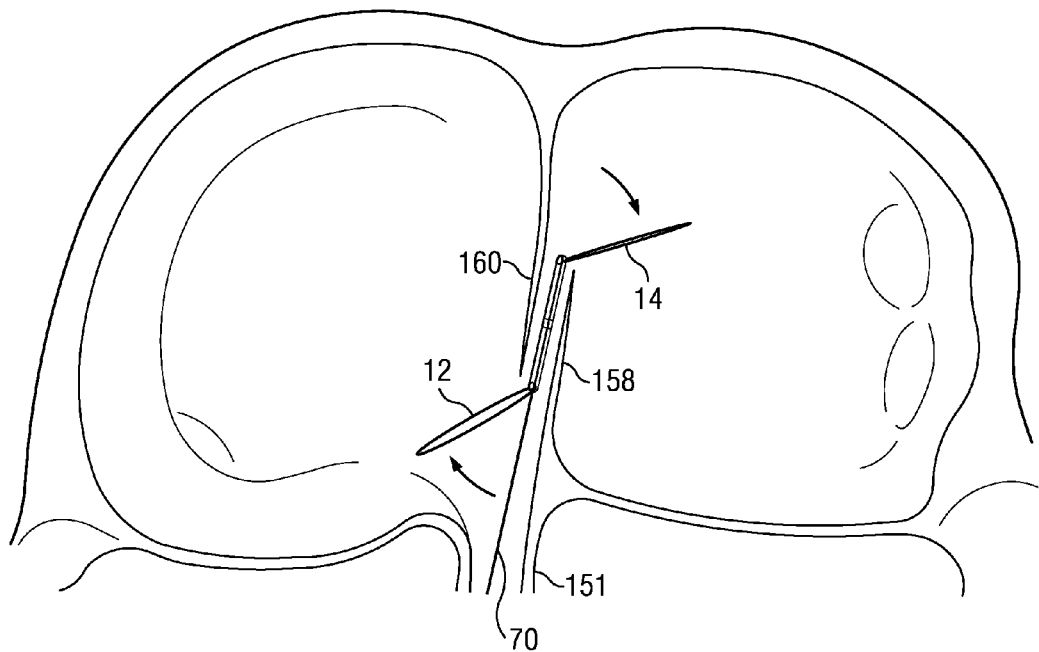
FIGS. 17-19 are schematic views illustrating the deployment of the first embodiment of the closure device within the atria.

Thus, as shown in FIG. 15, the wing 14 is delivered within the left atrium, the arms 16, 18 are delivered within the PFO track, and the wing 12 is delivered within the right atrium. The operator then rotates the outer tool 70 to rotate the closure device 10 such that the surfaces of the wings 12, 14 are parallel to the atrial septal plane as defined by the septum primum 158 and the septum secundum 160, as shown in FIG. 17.

Figure 16A:
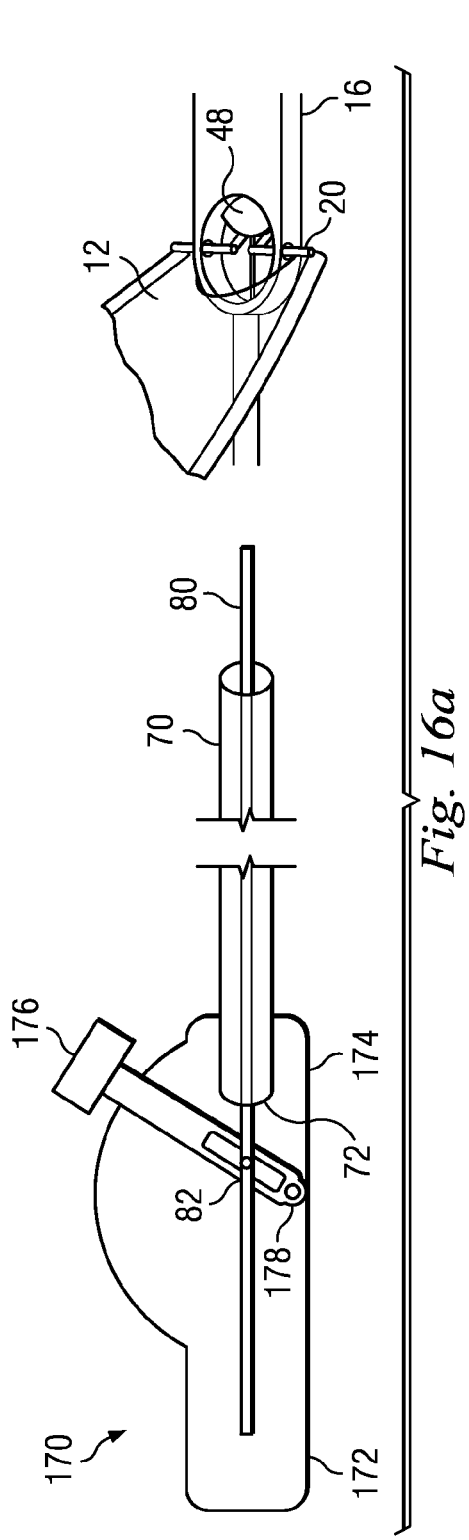
FIGS. 16a and 16b are partial cross-sectional view of a deployment handle accompanied by a perspective view of the hinge mechanism of the first wing during deployment of the wings.
Figure 16B:
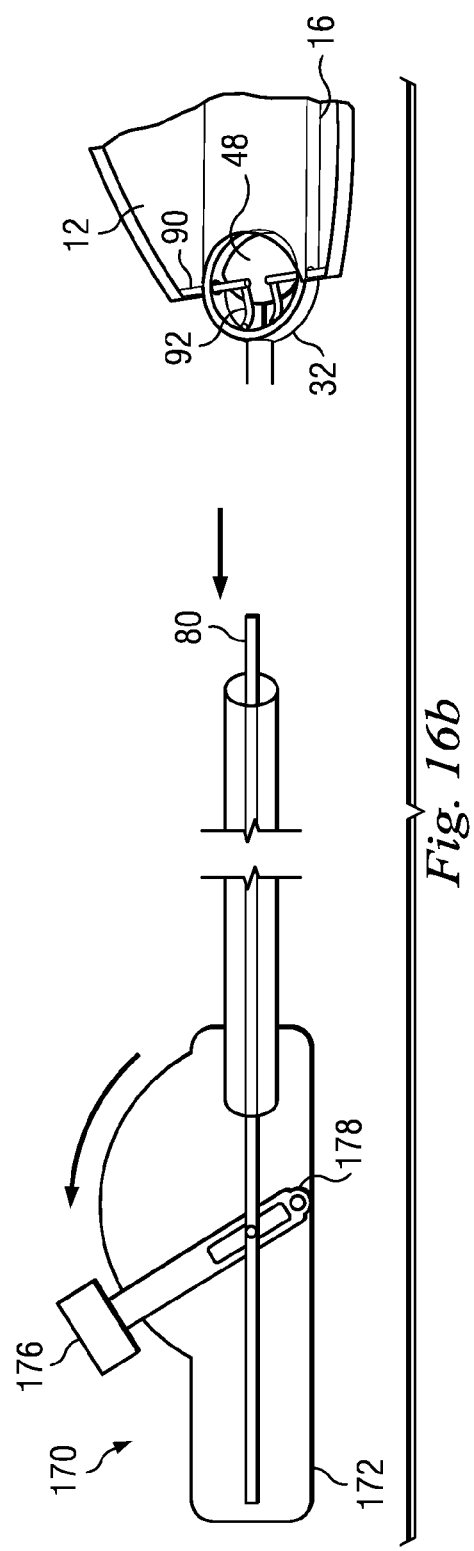

FIGS. 16a and 16b depict the physical mechanism by which the physician deploys the closure device 10. Deployment of the closure device 10 is directed by maneuvering the inner tool 80 within the outer tool 70. The physician controls the movements of the outer tool 70 and the inner tool 80 by using a deployment handle 170. As shown in FIG. 16a, the deployment handle 170 has a proximal end 172 and a distal end 174. The proximal end 72 of the outer tool 70 is fixedly attached to the distal end 174 of the deployment handle 170. The deployment handle 170 includes a deployment lever 176. The proximal end 82 of the inner tool 80 is fixedly attached to a swivel hinge 178 within the deployment lever 176.

As shown in FIG. 16b, when the physician pulls the deployment lever 176 towards the proximal end 172 of the deployment handle 170, the swivel hinge 178 rotates toward the proximal end 172, thereby pulling the inner tool 80 further inside the deployment handle 170 and causing the tab 48 of the arm 18 to slide within the passage 41 of the arm 16 toward the hinge mechanism 20.

Figure 18:
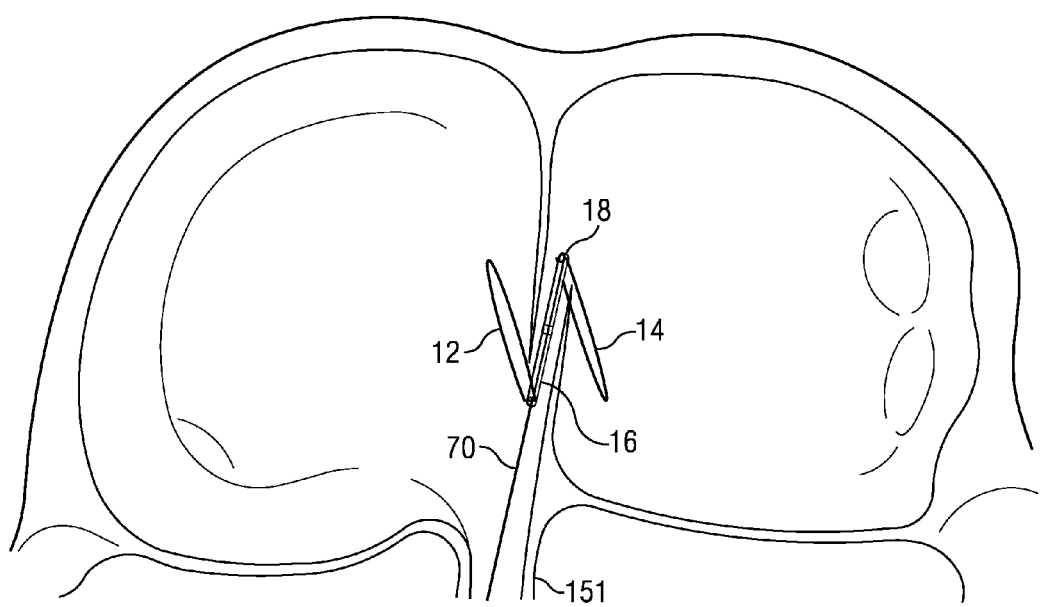
Figure 20A:
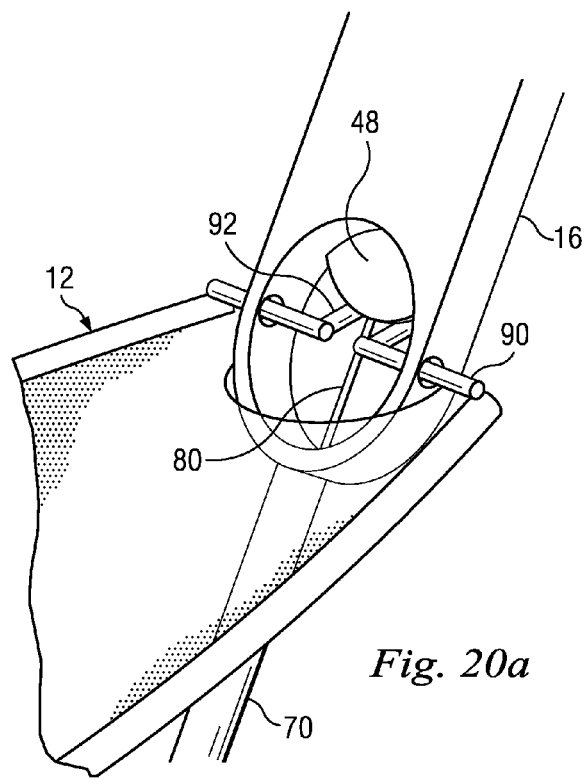
FIGS. 20a-20c are detailed perspective views illustrating the hinge mechanism of the first wing during deployment of the wings of the first embodiment of the closure device.
Figure 20B:
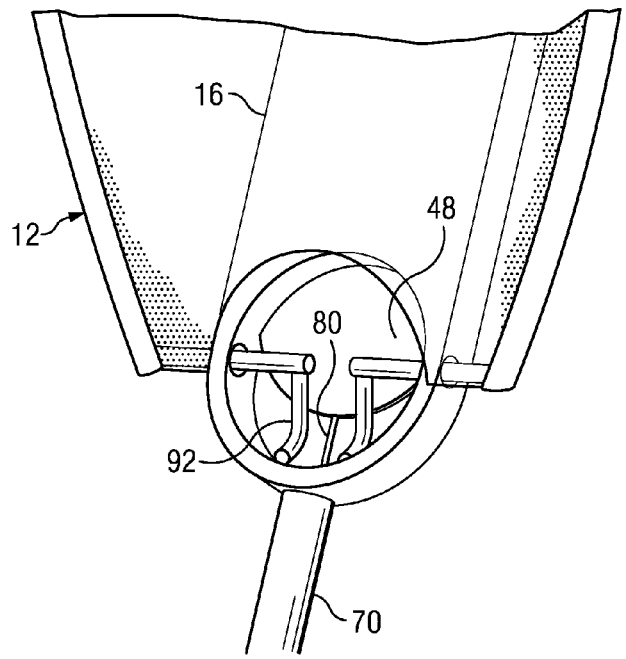

As shown in FIG. 20a, when the tab 48 is pulled by the inner tool 80 towards the hinge mechanism 20, the tab 48 contacts the convex portions of the hinge tips 92 and swivels the hinge tips 92 within the aperture 40 of the arm 16, causing the hinge pins 90 to rotate. As shown in FIGS. 17 and 20b, the rotation of the hinge pins 90 causes the simultaneous rotation of the wing 12 toward the arm 16. As the tab 48 slides into the passage 41, the arms 16, 18 interconnect with each other, causing the tab 38 of the arm 16 to simultaneously slide within the passage 51 of the arm 18 toward the hinge mechanism 22 (not shown). When the tab 38 of the arm 16 contacts the convex portions of the hinge tips of the hinge mechanism 22, the hinge tips swivel within the aperture 50 of the arm 18 and cause the hinge pins to rotate. The rotation of the hinge pins of the hinge mechanism 22 causes the simultaneous rotation of the wing 14 toward the arm 18, as shown in FIGS. 17 and 18.

Figure 19:
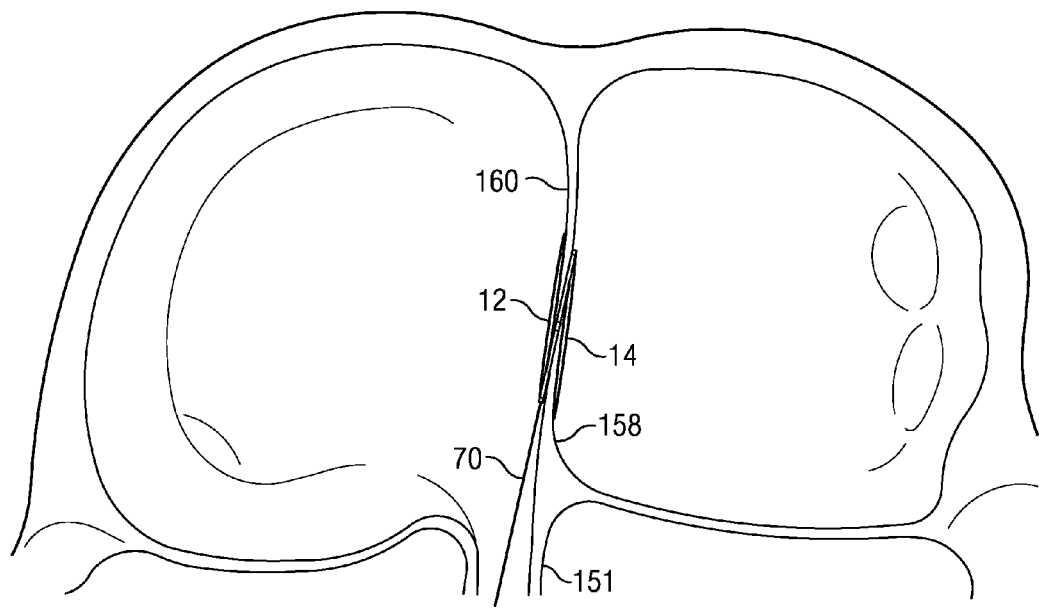
Figure 20C:
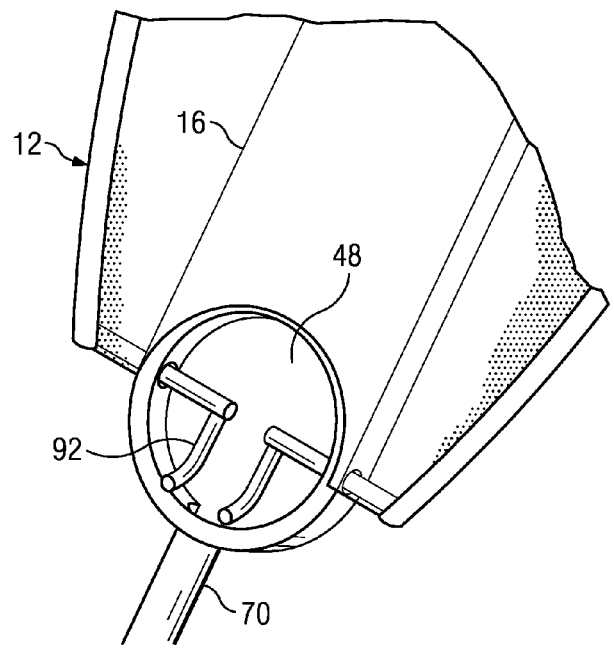

Further retraction of the inner tool 80 causes the tabs to further rotate the hinge tips. As shown in FIG. 19 and partially shown in FIG. 20c, when the tabs 38, 48 have advanced as far as possible within the passages 51, 41, respectively, the wing 12 swivels upward to press against the septum secundum 160 and the wing 14 swivels downward to press against the septum primum 158. In addition, when the tabs 38, 48 have advanced as far as possible within the passages 51, 41, respectively, the arms 16, 18 may be releasably interlocked together as described above, thereby locking the wing 12 against the septum secundum 160 and the wing 14 against the septum primum 158. It should be noted that the septum secundum 160 and the septum primum 158 do not have to be tightly touching along their entire lengths to effect proper closure of the PFO. Instead, it may be sufficient that the septum secundum 160 and the septum primum 158 are only brought close enough to allow tissue ingrowth to eventually seal the defect.

The physician may visually assess the delivery and deployment of the closure device by various methods including fluoroscopy, ultrasonography, and magnetic resonance imaging. For example, fluoro-visible dyes, such as radiopaque contrast, may be injected into the venous circulation and atria such that the venous vasculature and atrial chambers are visible using a fluoroscopic imaging device. Such a procedure, known as a type of venogram, allows the physician to localize a desired target location and to guide proper device positioning while performing the implantation procedure. In addition, an ultrasonic probe may be positioned in the patient's esophagus, within the patient's chest cavity, or on the patient's chest to image the heart. Moreover, the individual components of the closure device 10 and the delivery sheath 162 can include radiopaque fillers or markers that permit the physician to fluoroscopically visualize their location and orientation within the patient. Such radiopaque markers or fillers may be fabricated from noble metals such as platinum and gold, and may be attached to the closure device 10 using a variety of known methods such as adhesive bonding, lamination between two layers of polymers, or vapor deposition, for example.

After deploying the closure device 10 across the PFO track, the physician can reposition the closure device 10 by rotating, retracting, or advancing the outer tool 70 by rotating, retracting, or advancing the deployment handle 170 itself. After final positioning of the closure device 10, the inner tool 80 is disconnected from the closure device 10 by reverse threading the distal end 84 from the arm 18, the outer tool 70 is disconnected from the closure device 10 by reverse threading the distal end 74 from the arm 16, and both the inner tool 80 and the outer tool 70 are removed from the heart.

In some instances it may be necessary for the physician to remove the closure device 10 from the heart. For example, the physician may need to remove the closure device 10 from the heart if the closure device 10 is not appropriately sized for the particular PFO track 156 and/or if the closure device 10 cannot adequately seal the PFO track 156. The physician may use a suitable foreign body retrieval device, as is known in the art, to remove the closure device 10 from the heart. In some embodiments, the arm 16 has a retrieval formation such as a hook-like protrusion 96, as shown in FIG. 4, disposed on the body 36 at the end 32. The physician can retrieve the closure device 10 by using the foreign body retrieval device to snare or hook the arm 16 at the protrusion 96 and pull the arm 16 into a retrieval sheath. Pulling the arm 16 into the retrieval sheath will partially separate the arm 16 from the arm 18, thereby disengaging the locked hinge mechanisms 20, 22 and allowing the wings 12, 14 to swivel freely within the atria 152, 154, respectively. The physician can then pull the closure device 10 completely into retrieval sheath. As the physician retracts the wings 12, 14 into the retrieval sheath, the wings 12, 14 will assume compressed configurations. The physician can then retract the retrieval sheath to remove the entire closure device 10 from the patient's body.

In one exemplary aspect, the present disclosure is directed to a system for closing a patent foramen ovale (PFO) in a heart. The system may comprise a delivery catheter, a closure device, an outer tool, and an inner tool. The delivery catheter may have a lumen extending along a longitudinal axis. The closure device may be configured for delivery into the heart and for collapsible containment within the lumen. The closure device may comprise a first arm, a second arm, a first wing, and a second wing. The first arm may include a first body portion and a first tab portion, wherein the first body portion may include a first passage extending longitudinally therethrough. The second arm may include a second body portion and a second tab portion, wherein the second body portion may include a second passage extending longitudinally therethrough. The second passage may be sized to slidably receive the first tab portion and the first passage may be sized to slidably receive the second tab portion. The first wing may be pivotally connected to the first arm and the second wing may be pivotally connected to the second arm. The outer tool may be configured for attachment to the first body portion and have a lumen extending longitudinally through its length. The inner tool may be configured for attachment to the second tab portion. The lumen of the outer tool may be sized to receive a portion of the inner tool, wherein the inner tool is movable with respect to the outer tool to slide the second tab portion with respect to the first passage.

In another exemplary aspect, the present disclosure is directed to a system for closing a patent foramen ovale (PFO) in a heart. The system may comprise a delivery catheter, a closure device, an outer tool, and an inner tool. The delivery catheter may have a lumen extending along a longitudinal axis. The closure device may be configured for delivery into the heart and for collapsible containment within the lumen. The closure device may comprise a first arm and a second arm. The first arm may include proximal and distal ends, wherein the proximal end is pivotally connected to a first wing via a first hinge and the first hinge includes a first projection. The second arm may include proximal and distal ends, wherein the proximal end is pivotally connected to a second wing via a second hinge and the second hinge includes a second projection. The distal end of the first arm may be configured to engage the second projection to pivot the second wing with respect to the second arm, and the distal end of the second arm may be configured to engage the first projection to pivot the first wing with respect to the first arm. The outer tool may be configured for attachment to the proximal end of the first arm and have a lumen extending longitudinally through its length. The inner tool may be configured for attachment to the distal end of the second arm. The lumen of the outer tool may be sized to receive a portion of the inner tool, wherein the inner tool is movable with respect to the outer tool to slide the distal end of the second arm with respect to the first hinge.

The devices, systems, and methods described herein provide an improved and more efficient system of PFO closure. Applicants note that the procedures disclosed herein are merely exemplary and that the services and methods disclosed herein may be utilized for numerous other medical processes and procedures. Although several selected embodiments have been illustrated and described in detail, it will be understood that they are exemplary, and that a variety of substitutions and alterations are possible without departing from the spirit and scope of the present invention, as defined by the following claims.

We claim:

1. A device for closing a patent foramen ovale (PFO), the device comprising:
   a first arm, the first arm including a first body portion and a first tab portion, the first body portion including a first passage extending longitudinally therethrough;
   a second arm, the second arm including a second body portion and a second tab portion, the second body portion including a second passage extending longitudinally therethrough, wherein the second passage is sized to slidably receive the first tab portion and the first passage is sized to slidably receive the second tab portion;
   a first wing pivotally connected to the first arm; and
   a second wing pivotally connected to the second arm.

2. The device of claim 1 wherein the first body portion and the first tab portion are rigidly connected.

3. The device of claim 1 wherein the first wing is pivotally connected to the first arm by a first hinge and the second wing is pivotally connected to the second arm by a second hinge.

4. The device of claim 3 wherein the first hinge includes a first projection and the second hinge includes a second projection, the first tab portion is configured to engage the second projection to swivel the second wing with respect to the second arm, and the second tab portion is configured to engage the first projection to swivel the first wing with respect to the first arm.

5. The device of claim 4 wherein the first tab portion is configured to swivel the second projection and second tab portion is configured to swivel the first projection.

6. The device of claim 4 wherein the first body portion includes a first aperture, and the first projection is rotatable within the first aperture.

7. The device of claim 1 including a locking mechanism for restricting movement of the first tab portion with respect to the second passage.

8. The device of claim 7 wherein the locking mechanism includes interlocking ridges formed on the first tab portion and the second passage.

9. The device of claim 1 wherein the first and second wings each include a biocompatible membrane.

10. The device of claim 1 wherein the first and second wings each include a shape memory frame.

11. The device of claim 1 wherein the first and second wings each have an expanded configuration with an elliptical shape.

12. The device of claim 1 including a first tool configured for attachment to the first body portion and a second tool configured for attachment to the second tab portion, wherein the first tool is movable with respect to the second tool to slide the second tab portion with respect to the first passage.

13. The device of claim 12 wherein the first tool includes an inner lumen sized to receive a portion of the second tool.

14. The device of claim 1 wherein the first body portion of the first arm includes a protrusion such that a retrieval device releasably attaches to the protrusion and exerts a pulling force on the first arm to withdraw the device from the PFO.

15. A device for closing a patent foramen ovale (PFO), the device comprising:
   a first arm with proximal and distal ends, the proximal end pivotally connected to a first wing via a first hinge, the first hinge including a first projection; and
   a second arm with proximal and distal ends, the proximal end pivotally connected to a second wing via a second hinge, the second hinge including a second projection,
   wherein the distal end of the first arm is configured to engage the second projection to pivot the second wing with respect to the second arm and the distal end of the second arm is configured to engage the first projection to pivot the first wing with respect to the first arm.

16. The device of claim 15 wherein the proximal end of the first arm includes a first passage extending longitudinally therethrough, the proximal end of the second arm includes a second passage extending longitudinally therethrough, and wherein the first passage is sized to slidably receive the distal end of the second arm and the second passage is sized to slidably receive the distal end of the first arm.

17. The device of claim 16 wherein the distal portion of the second arm contacts the first hinge to direct rotation of the first wing toward the first arm, and the distal portion of the first arm contacts the second hinge to direct rotation of the second wing toward the second arm.

18. The device of claim 16 including a locking mechanism for restricting movement of the distal portion of the first arm with respect to the second passage.

19. The device of claim 18 wherein the locking mechanism includes interlocking ridges formed on the distal portion of the first arm and the second passage.

20. The device of claim 15 wherein the first and second wings each include a biocompatible membrane.

21. The device of claim 15 wherein the first and second wings each include a shape memory frame.

22. The device of claim 15 wherein the first and second wings each have an expanded configuration with an elliptical shape.

23. The device of claim 15 including a first tool configured for attachment to the proximal end of the first arm and a second tool configured for attachment to the distal end of the second arm, wherein the first tool is movable with respect to the second tool to slide the distal end of the second arm with respect to the first arm.

24. The device of claim 23 wherein the first tool includes an inner lumen sized to receive a portion of the second tool.

25. The device of claim 15 wherein the proximal end of the first arm includes a protrusion such that a retrieval device releasably attaches to the protrusion and exerts a pulling force on the first arm to withdraw the device from the PFO.

* * * * *